United States Patent [19]

Cohen et al.

[11] Patent Number: 5,162,652

[45] Date of Patent: Nov. 10, 1992

[54] METHOD AND APPARATUS FOR RAPID DETECTION OF CONTRABAND AND TOXIC MATERIALS BY TRACE VAPOR DETECTION USING ION MOBILITY SPECTROMETRY

[75] Inventors: Martin J. Cohen, West Palm Beach; Roger F. Wernlund, Lake Worth; Robert M. Stimac, Palm Beach Gardens, all of Fla.

[73] Assignee: PCP, Inc., West Palm Beach, Fla.

[21] Appl. No.: 742,646

[22] Filed: Aug. 7, 1991

[51] Int. Cl.$^5$ ............................................. H01J 49/04
[52] U.S. Cl. ................... 250/288; 73/863.21; 73/863.33; 73/863.83; 73/863.84; 73/864.62; 73/864.83
[58] Field of Search ............ 250/288; 73/864.62, 73/863.21, 863.12, 864.83, 864.84, 863.33, 863.83, 863.84

[56] References Cited

U.S. PATENT DOCUMENTS 3,357,257 12/1967 Herndon et al. ............... 73/863.33
4,818,870 4/1989 Griffiths ......................... 250/288
4,909,089 3/1990 Achter et al. ................. 73/863.83

Primary Examiner—Jack I. Berman
Attorney, Agent, or Firm—Schweitzer Cornman & Gross

[57] ABSTRACT

An apparatus and method for the detection and identification of the presence of chosen molecules, typically toxic or contraband located within sealed luggage and the like, comprises subjecting the sealed luggage to a process whereby a portion of the enclosed atmosphere within the luggage is extracted and combined with the surrounding atmosphere in a closed chamber. The extracted, combined sample is passed to a collector, typically a molecule adsorber, which concentrates the chosen molecules by collection on a collecting surface. After the end of a collection period, the adsorbed molecules are released from the surface and passed to an identifier, such as an ion mobility spectrometer. By use of appropriate collection and valving elements, analysis can be accomplished quickly and accurately for a large number of luggage items or the like subject to examination.

44 Claims, 19 Drawing Sheets

BAGGAGE EXAMINER SCHEMATIC DIAGRAM

BLOCK DIAGRAM OF SINGLE VAPOR COLLECTOR IN AN ARRAY OF TEN UNITS

| FUNCTION | STEP | TIME (SEC) | BAG DOORS | PISTON | MODULE PRESSURE PSIG | VAPOR COLLECTOR STATUS | MODULE FAN | VACUUM VALVE | PRESSURE VALVE | OPEN-TO-AIR VALVE | VAPOR COLLECTOR TO MODULE VALVES | SENSOR VALVES |
|---|---|---|---|---|---|---|---|---|---|---|---|---|
| LOADING | 1 | 6 | LOAD/OPEN | UP | ATM | COOLING | ON | CLOSED | CLOSED | OPEN | OPEN | CLOSED |
| VAPOR EXTRACTION AND COLLECTION | 2 | 12 | CLOSED | MOVES DOWN | +2 PSIG | COOLING | ON | CLOSED | CLOSED | OPEN | OPEN | CLOSED |
| | 3 | 18 | CLOSED | UP/DOWN | +2 PSIG | COOLING | ON | OPEN/CLOSED | CLOSED/OPEN | CLOSED | OPEN | CLOSED |
| | 4 | 24 | CLOSED | UP/DOWN | +2 PSIG | COOL | ON | OPEN/CLOSED | CLOSED/OPEN | CLOSED | OPEN | CLOSED |
| | 5 | 30 | CLOSED | UP/DOWN | +2 PSIG | COOL | ON | OPEN/CLOSED | CLOSED/OPEN | CLOSED | OPEN | CLOSED |
| | 6 | 36 | CLOSED | UP/DOWN | +2 PSIG | COOL | ON | OPEN/CLOSED | CLOSED/OPEN | CLOSED | OPEN | CLOSED |
| | 7 | 42 | CLOSED | UP/DOWN | +2 PSIG | COOL | ON | OPEN/CLOSED | CLOSED/OPEN | CLOSED | OPEN | CLOSED |
| | 8 | 48 | CLOSED | UP/DOWN | +2 PSIG | COOL/HEAT | ON | OPEN/CLOSED | CLOSED/OPEN | CLOSED | CLOSED | CLOSED |
| SENSING | 9 | 54 | CLOSED | MOVES UP | ATM | HOT | ON | CLOSED | CLOSED | OPEN | CLOSED | OPEN |
| UNLOADING | 10 | 60 | UNLOAD/OPEN | UP | ATM | COOLING | ON | CLOSED | CLOSED | OPEN | OPEN | CLOSED |

FIG. −6  TYPICAL STEPS IN BAGGAGE EXAMINATION IN A SINGLE MODULE

FIG.—9

EXPLOSIVE VAPOR COLLECTOR (PACKAGE SCHEMATIC)

ARRAY OF 10 EXPLOSIVE VAPOR COLLECTORS & ROTARY VALVE PATTERN

TEMPERATURE, GAS FLOW & POWER PROFILES OF VAPOR COLLECTOR

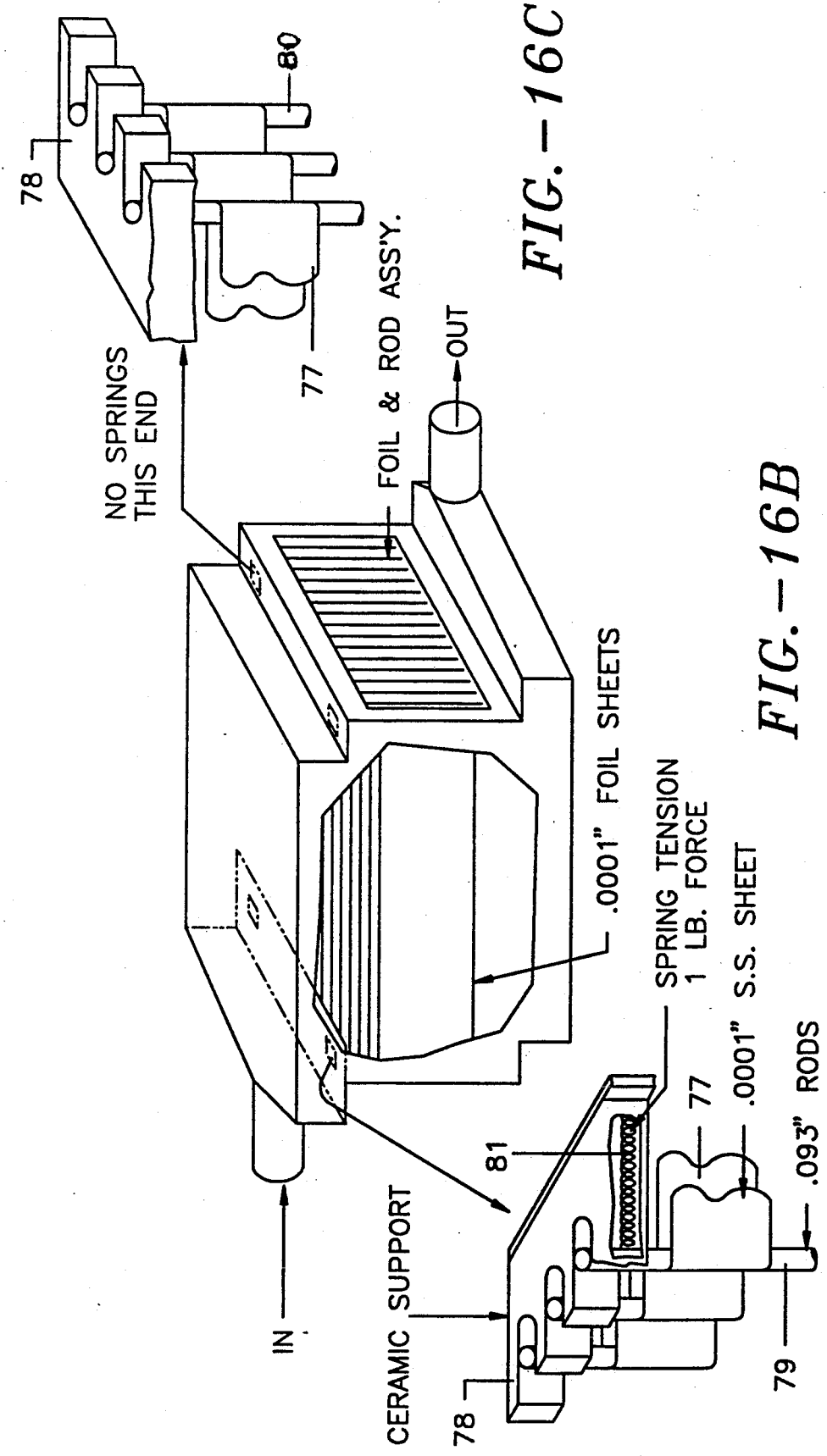

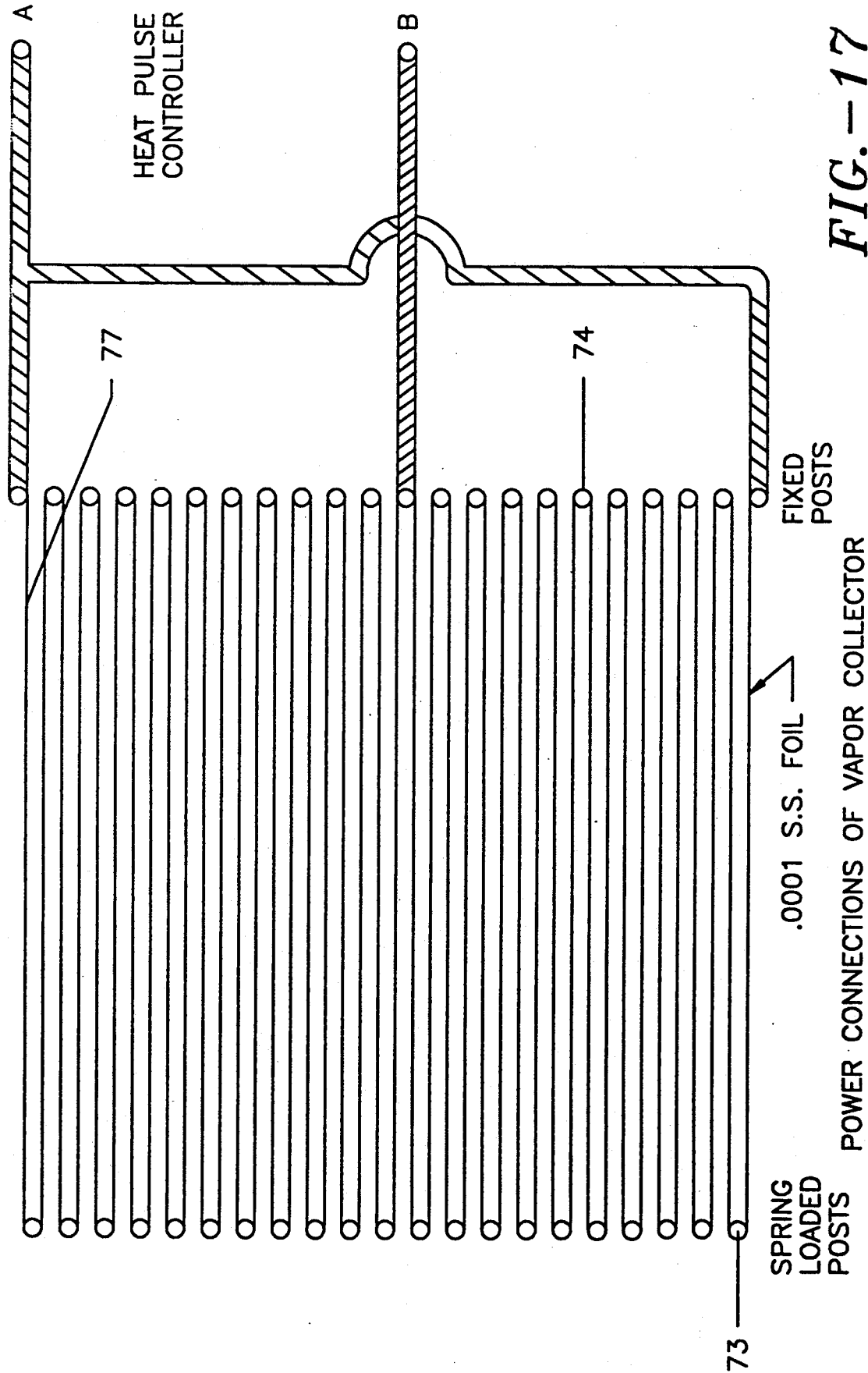

HEAT PULSE CONTROLLER (WITH TRANSFORMER)

HEAT PULSE CONTROLLER (WITHOUT TRANSFORMER)

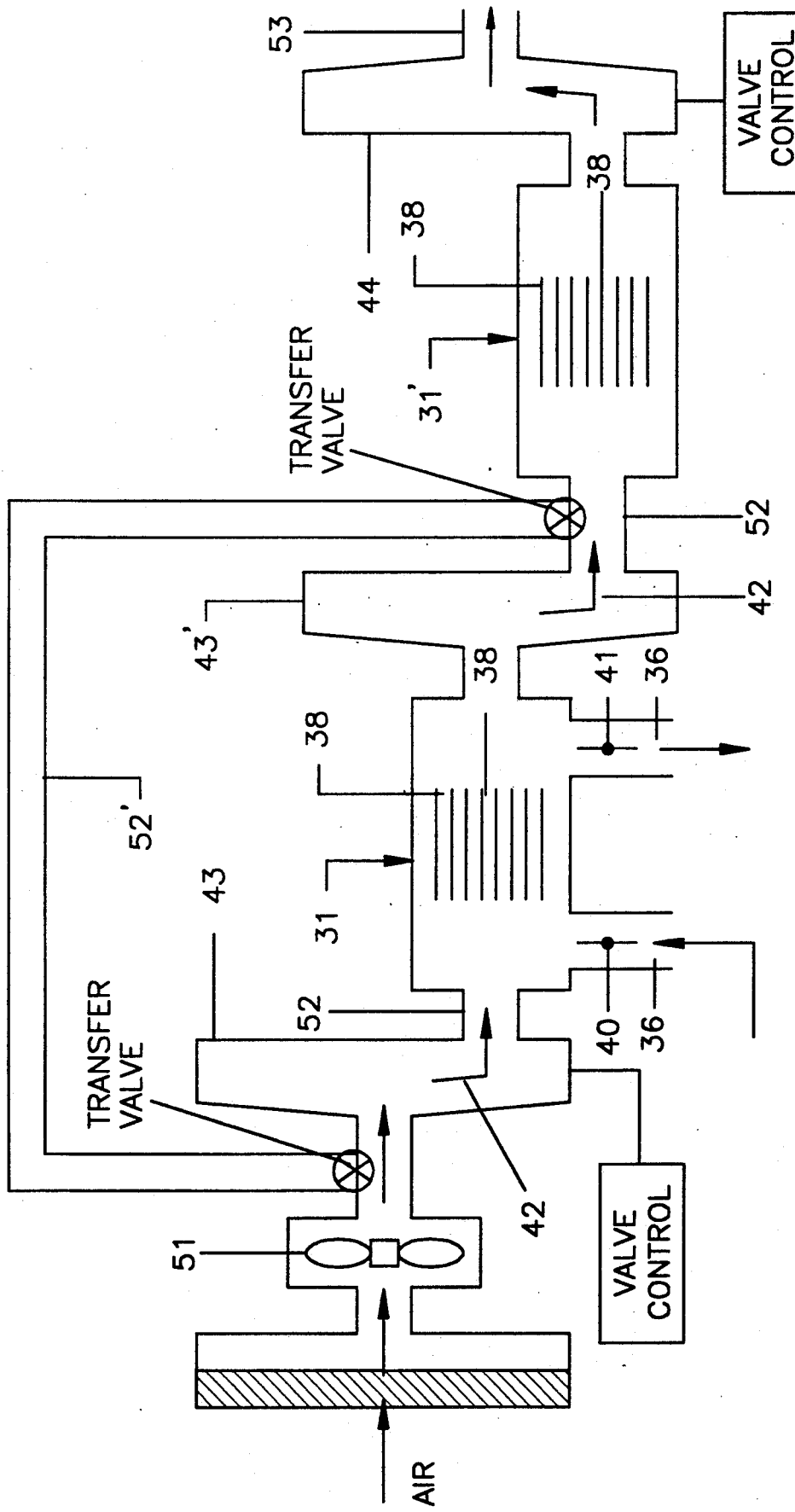

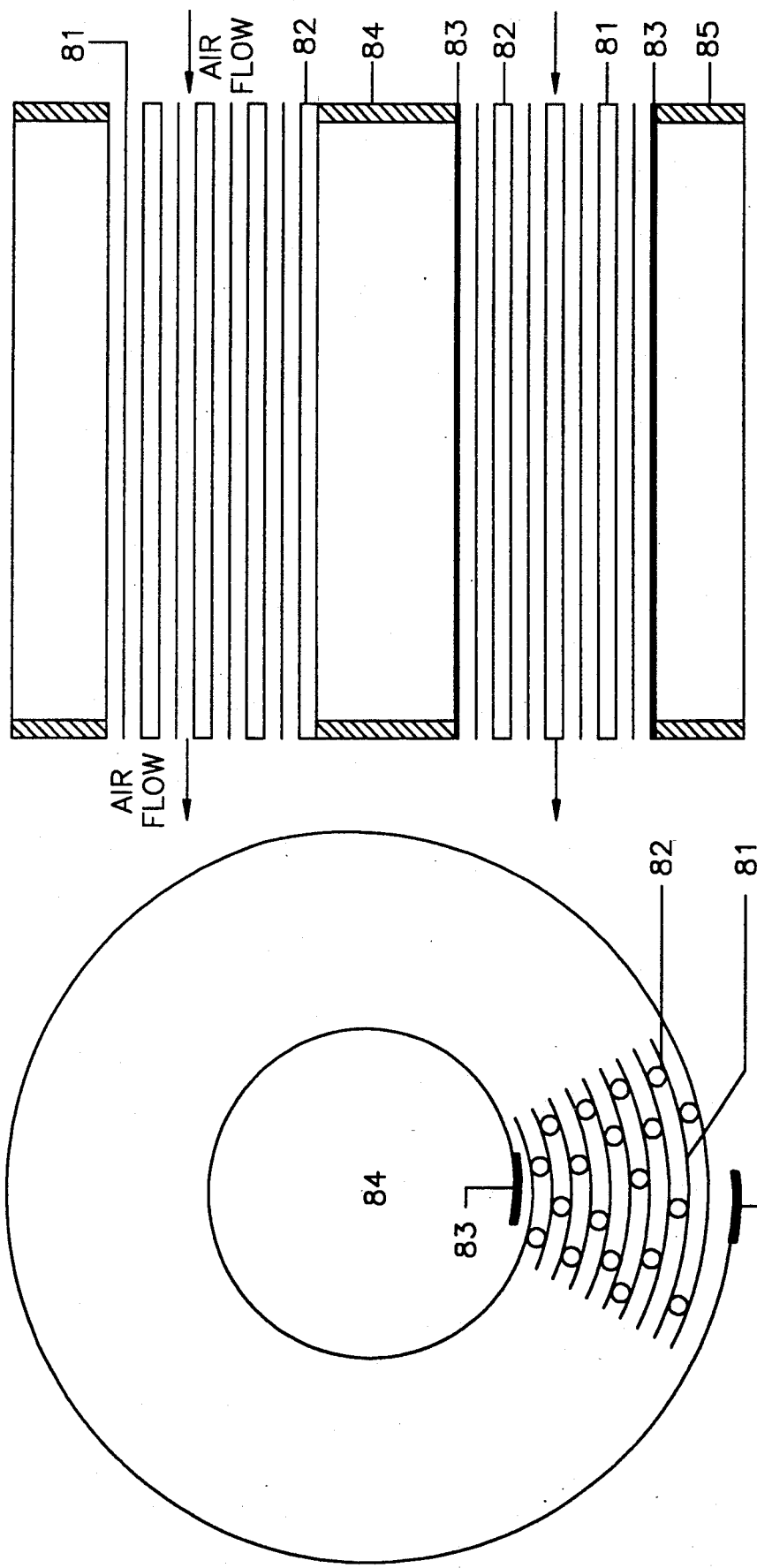

METHOD AND APPARATUS FOR RAPID DETECTION OF CONTRABAND AND TOXIC MATERIALS BY TRACE VAPOR DETECTION USING ION MOBILITY SPECTROMETRY

BACKGROUND OF THE INVENTION

Ion mobility spectrometry, heretofore referred to as plasma chromatography in the technical and patent literature, has evolved into a tool having important application in the field of vapor detection and analysis. The applicants' early work in this field is disclosed, inter alia. in U.S. Pat. Nos. 3,699,333; 3,526,137; 3,593,018; 3,596,088; 3,621,239; 3,621,240; 3,624,389; 3,626,178; 3,626,179; 3,262,180; 3,262,181; 3,262,182; 3,629,574; 3,639,757; 3,668,381; 3,668,383; 3,668,385; 3,697,748; 3,697,749; 3,742,213; 3,812,355; 3,845,301; and, 4,195,513.

The extraction of vapor samples from luggage to detect explosives has been the subject of research and development in the U.S. Department of Transportation and others.

The subject matter of the present invention encompasses several improvements in Ion Mobility Spectrometer (hereinafter sometimes abbreviated as IMS) instrumentation for special applications in detecting high molecular weight explosive vapors, illegal drug vapors, or contaminants such as carcinogens and dioxins by sophisticated "sniffing" and analyzing apparatus. Condensible vapors, aerosols, chlorinated fluorocarbons, and fine particulates also may be collected and analyzed for the presence of illegal or dangerous substances.

The Model LRV-1 IMS instrument of PCP, Inc., West Palm Beach, Florida, is the basis for a new and improved large reaction volume IMS system (LRVIMS) of superior response and air flow characteristics, which will, in conjunction with other features, be described in the following detailed description of the invention.

The "new detection concepts" and both new instrument system features using the Ion Mobility Spectrometer will be described hereinafter especially with reference to detection of explosive vapors, such as TNT and RDX, in airport screening applications seeking to detect explosives hidden in baggage or on passengers.

BRIEF SUMMARY OF THE INVENTION

The fundamental elements of the baggage examination system of the present invention comprise the following:

A. Baggage loader/unloader apparatus;

B. A series of modules for baggage examination, each module comprising:

1. Two contiguous compartments, each air-tight and separated by a hollows-sealed piston, preferably oriented in a vertical array. The upper compartment has vacuum and pressure control valves. Doors for baggage pass-through are located in the lower compartment; and 2. A blower for air circulation through the baggage compartment and to a dedicated vapor collector.

C. A vapor collector array package for the series of modules comprising:

1. Vapor collectors for each module;
2. an air filter;
3. a blower;
4. multi-port rotary valves (one port per collector);
5. a multi-unit heating control circuit; and
6. a passage to a vapor sensor.

D. A vapor sensor (Large Reaction Volume Ion Mobility Spectrometer) comprising:

1. A large reaction volume cell, typically having a threshold response at $5 \times 10^{-14}$ parts and a signal-to-noise ratio of 2 for the targeted explosives (TNT, RDX, etc.) with a six second time constant.

2. Ancillary equipment, including a vacuum/pressure pump and storage tanks, a blower, and vacuum and pressure tanks.

E. A control system for controlling the baggage loader/unloader; baggage examination cycle timing, the vapor collectors, and sensors having appropriate signal readout.

The foregoing elements are coupled together such that the baggage loader/unloader deposits an item of baggage within the lower section of an examination module. The pressure within the lower compartment is modulated to cause extraction of vapors from the baggage interior into the compartment, which vapors are swept from the compartment to a vapor collector, where they are collected.

After collection, the vapors are released by the collector and are passed to a sensor spectrometer for analysis. The presence of a targeted vapor activates the control circuitry to isolate and/or retest the source baggage as required and to alert operating personnel.

In a preferred embodiment, multiple modules operate in parallel in connection with a single sensor to provide improved throughput as opposed to a single detection system. Such a system may also include a plurality of detection stations for individuals, in which a stream or curtain of air is directed across the individual to sweep any vapors from target compounds hidden on the person or in carried luggage. The vapors are collected and analyzed identically to those collected from baggage.

A more complete understanding of the present invention can be accomplished upon reference to the following detailed description taken in conjunction with the accompanying drawings.

DESCRIPTION OF THE DRAWINGS

FIG. 4A is a schematic representation of air circulation through the module of FIG. 4;

FIG. 6 is a table setting forth the steps employed in a sixty second cycle for baggage examination in accordance with the principles of the invention;

FIGS. 16A, 16B and 16C are perspective views of the construction of an alternate vapor collector design in accordance with the principles of the invention;

FIG. 17 is a plan view of the power connections for the vapor collector design of FIG. 16;

FIG. 19 is a schematic of a cascade arrangement for a multiple adsorber system;

FIG. 20A is an end view of an alternative vapor collector; and

FIG. 20B is a side view thereof.

DETAILED DESCRIPTION OF THE INVENTION

Overall System Concepts

Figure 1:
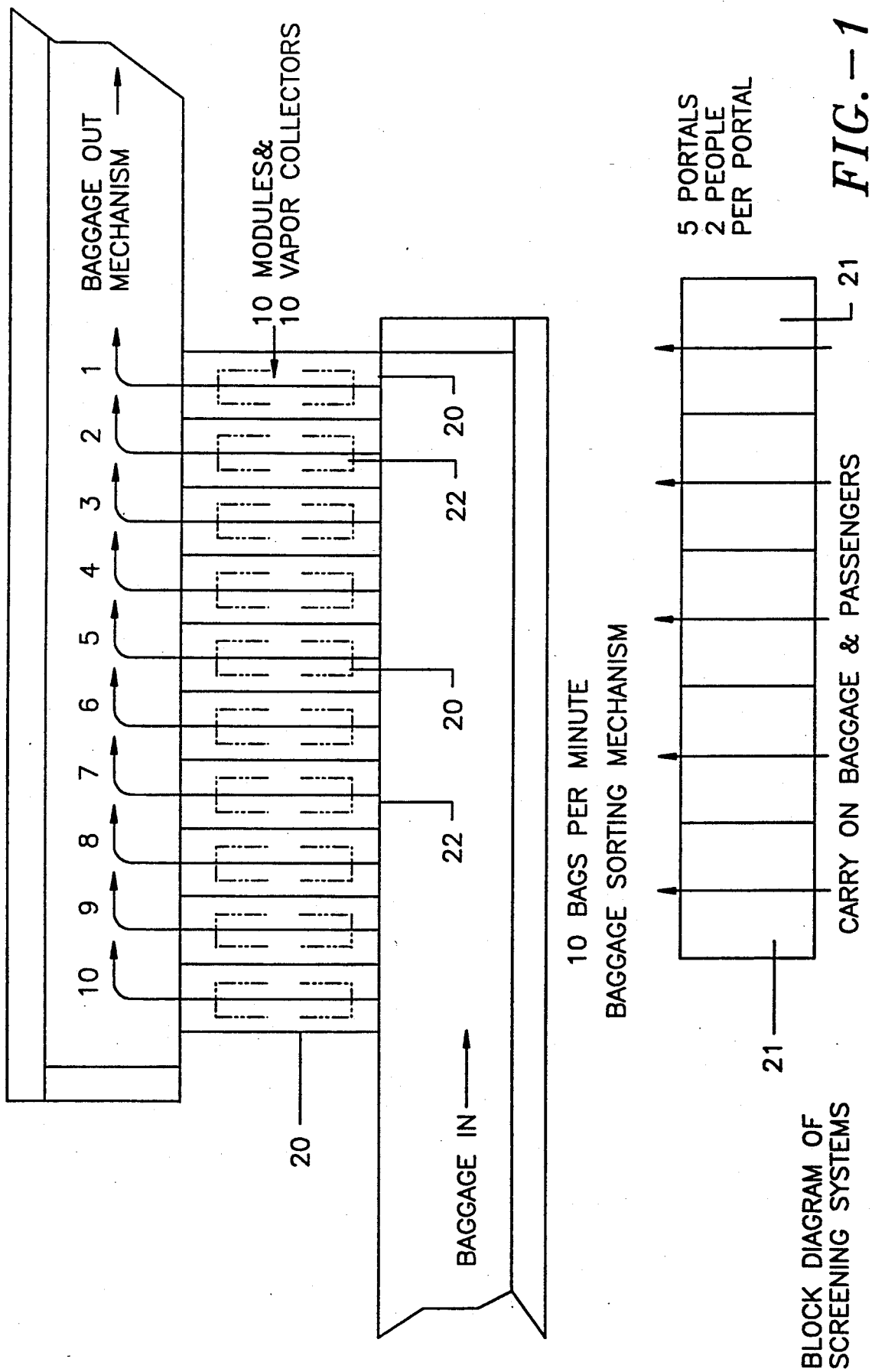
FIG. 1 is a schematic diagram showing the fundamental screening system for baggage and passengers embodying the principles of the invention.
Figure 2:
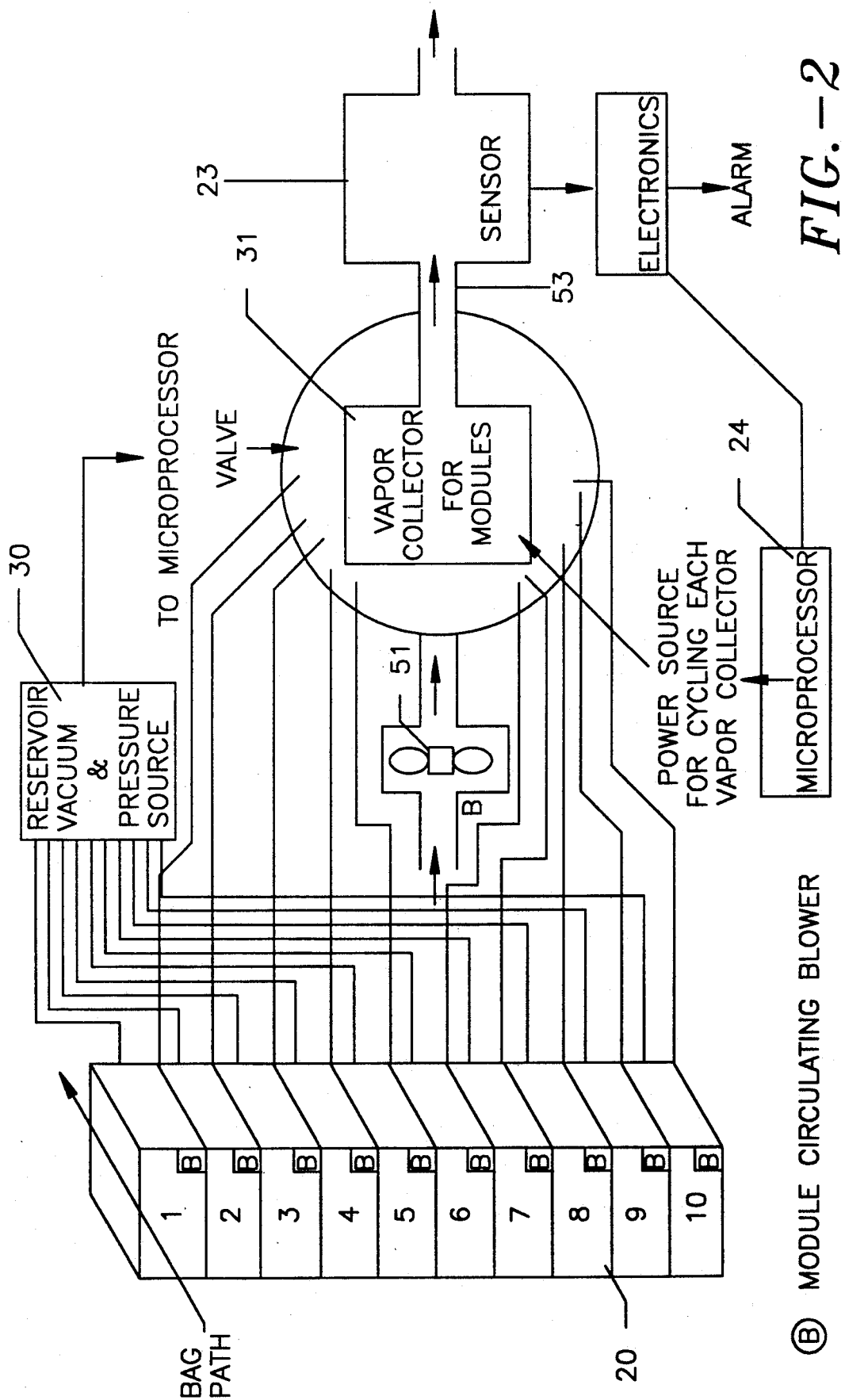
FIG. 2 is a schematic diagram showing the baggage examination apparatus of the present invention.

The overall system concept for both checked baggage/cargo and carry-on baggage and passengers is illustrated in FIGS. 1 and 2 and includes ten checked baggage examination modules 20 and five passthrough portals 21 for passengers and carry-on baggage. Ten vapor collectors 22 are provided for checked baggage; five units for carry-on baggage and passengers (not shown) are similarly employed. A central baggage sensor instrument 23 receives the vapors, with the system being monitored and controlled by microprocessor 24. A similar sensor/microprocessor system is utilized for the carry-on baggage/passenger system.

The elements of a full system embodying the invention include an automatic baggage loader/unloader, and control system, as well as other utility hardware. For checked baggage with the automatic baggage loader/unloader, an objective of screening ten bags per minute is reliably reached. For passenger and carry-on baggage screening, five portals are used with two passengers per portal per minute, i.e., ten passengers per minute.

The novel use of a dedicated stationary explosive vapor collector permits operation of the baggage examination modules to remove the available target explosive vapor from the baggage with minimal loss of vapor due to adhesion to the walls of the sensor chamber, as well as with optimum performance of the sensor. Accordingly, each element may be more easily designed and operated for high performance.

Baggage Examiner System Design

Figure 3:
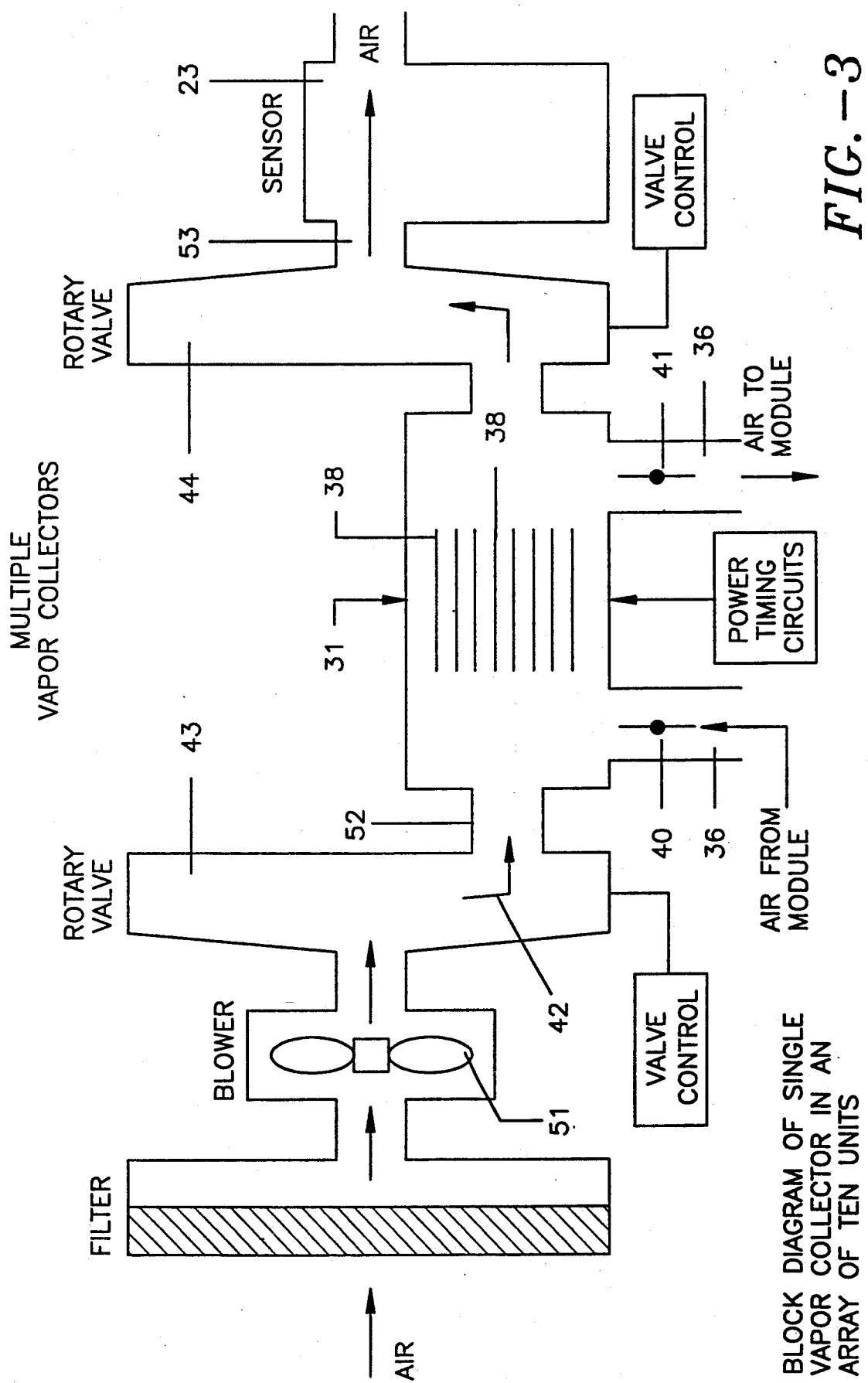
FIG. 3 is a diagrammatic representation of a vapor collector of the invention.

The basic vapor-handling elements of the automatic baggage examiner include a group of ten stationary baggage examination modules 20 (in array), which may be constructed in various sizes and shapes to accommodate differing sizes of luggage. Loading and unloading occurs at the rate of ten bags per minute. Each item of luggage passes through a module (the ten modules filling in sequence), and each resides in the module for sixty seconds, which includes preparation and recovery time as well as actual sampling time. Each of the ten modules is served by a dedicated stationary vapor collector (FIG. 3). These ten stationary vapor collectors are proximate to a single sensor. Loading and unloading the baggage is effected by an automatic conveyor or comparable materials handling apparatus.

Checked Baggage Examination Module

Figure 4:
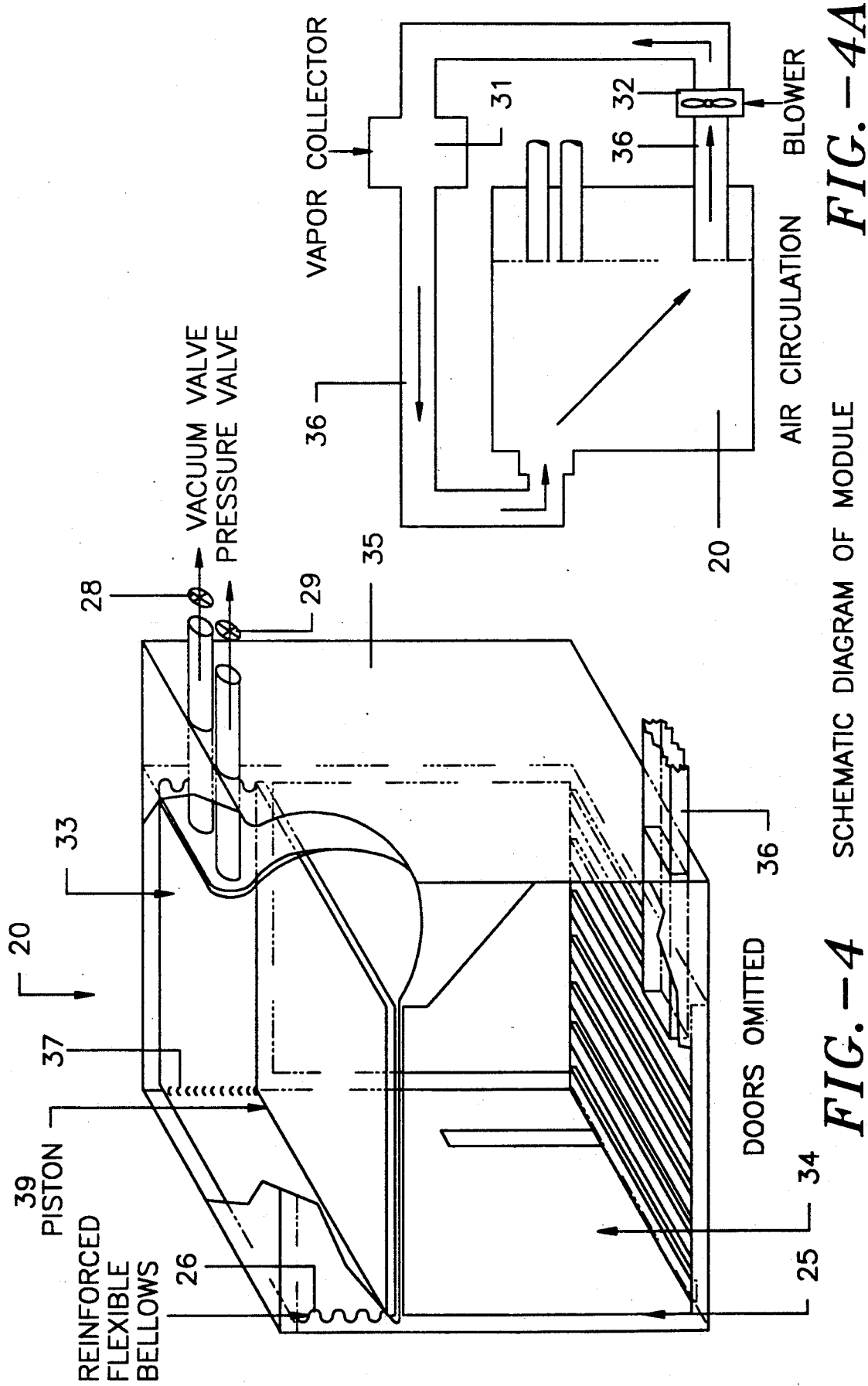
FIG. 4 is a schematic perspective view of a baggage examining module.

As will be appreciated, the baggage module 20 (FIG. 4) is an essential element of the invention for the efficient extraction of the target vapor material. The functions and features of the module are as follows:

(a) An entrance/exit aperture with two sealable doors for loading/unloading of baggage in a pass-through pattern;

(b) a piston-type movable wall with flexible supported bellows to divide the module into two chambers and to support a partial vacuum and pressure of up to $\pm 0.2$ atmospheres. The lower baggage section chamber is sealed from the upper vacuum/pressure section chamber A baggage accepting volume of $2\text{-}\frac{1}{2} \times 2\text{-}\frac{1}{2} \times 2\text{-}\frac{1}{2}$ feet or larger is preferred.

(c) a vacuum valve 28 to a vacuum tank and a pressure valve 29 to a compressed air tank;

(d) a dedicated stationary vapor collector 31 (adsorber/desorber);

(e) A fan/blower 32 to circulate the air frequently through the module and vapor collector at flow rates up to 100 cubic feet per minute;

(f) a connection to the vapor collector (FIG. 3); and (g) Vacuum/pressure controls and air release valves.

The module 20 itself consists of upper and lower compartments 33,34, air-tight during the target vapor extraction part of the cycle. The outer walls/doors 35 of the module are strong enough to withstand the vacuum/pressure extremes which are developed. The vapor/collector air path 36 is air-tight since it is part of the target vapor enclosure.

With the array of ten modules, ten bags may be loaded, sampled, and unloaded every minute. The examination cycle of sixty seconds includes twelve seconds for loading and unloading, forty-two seconds for vapor extraction and collecting, and six seconds for actual sensing of the vapor (FIG. 6).

Vapor extraction is effected by oscillating the module pressure above and below atmospheric pressure by displacing the common wall 39 (piston) of the module. Specifically, the piston wall is moved toward the baggage, still at atmospheric pressure, using a capacitance proximity sensor or other positioning means. The lower compartment 34 is then sealed. The piston wall is moved to increase the volume of the lower compartment by opening the vacuum valve 28, drawing the piston wall 39 upwardly, and thus reducing the pressure in the lower chamber. A ten percent (10%) change in module volume will cause a 1.5 psig change in pressure. The ga inside the bag intended to be sampled will diffuse out through the bag sides, carrying the target vapor. The pressure in the lower chamber is oscillated from ten percent (10%) below atmospheric pressure to ten percent (10%) above atmospheric pressure by a preferred cycle of approximately five strokes during the vapor extraction period. While these oscillations are occurring, the module air is recirculating over the bag and through the vapor collector. The target vapor is continuously adsorbed by the vapor collector. For this reason, very little of the expelled vapor will be returned to the bag in the compression portion of the oscillating cycle.

The specific vacuum pressure cycle is set by using a standard capacitance manometer with dual pressure set points referenced to atmosphere. Appropriately regulated timing circuits and flow valves associated with the vacuum and pressure tanks control the period and magnitude of piston oscillation as required.

Explosive Vapor Collector

Referring to FIG. 3, one vapor collector 31, having a series of plates 38, is dedicated for use with each module 20 and is located adjacent to the sensor 23. The sampled target vapor is sucked from the bag by the pressure/vacuum, developed in the baggage chamber and circulates through the collector for forty-two seconds. The vapor collector 31 is cool during this phase of operation and well adsorbs the sampled target vapor removed from the luggage being screened.

The vapor collector experiences gas density changes during the vacuum-pressure oscillation. Since the adsorption is diffusion dominated, the average pressure is used in the subsequent analysis for detecting an explosive.

The closed air circulation through the baggage module and vapor collector is not filtered. The vapor collector is operated with its plates 38 in a vertical plane; air flows from top to bottom to minimize dust collection. After the collection period is completed, the vapor collector is sealed off from the baggage module by closing its two valves 40, 41. The collector is then instantly heated (in less than one second) to about 200° C., to volatilize the sampled vapor. The heating occurs immediately upstream of a connection to the separate flow of filtered air 42, which is directed to the sensor 23. A pair of rotary valves 43, 44 sequentially couple each collector to a source of filtered air generated by blower 51 and the sensor 23. The evolved surge of target vapor is carried by this separate air flow of filtered air out of the collector and through the sensor for analysis during a six second period.

Adequate heater power continues to be applied during the six second sensing period to complete the evolution of the vapor. At the end of this period, the heat is discontinued and the vapor collector is closed from the sensor air flow by the rotary valves and opened to the module circulating air for cooling. Cooling occurs during the baggage loading and unloading steps for a period of twelve seconds.

The vapor collector 31 thus functions as an "Explosive Vapor Generator" (EVG) which produces low vapor concentrations typically in $10^{-14}$ parts, at an in flow of 10 to 15 cubic feet per minute, at temperatures of 140° C. to 180° C. and represents an important feature of the invention.

Explosive Vapor Sensor—Large Reaction Volume IMS

In accordance with the invention, the sensor 23 is in the form of a new and improved Large Reaction Volume Ion Mobility Spectromete (LRVIMS) and it is employed as a key element in the new method and apparatus. This unit (FIG. 5) has a reaction volume, 20 cm $\times$ 20 cm $\times$ 20 cm; air flow of 600 liters per minute (20 cu.ft./per min.); a threshold signal for S/N=2 (TNT, RDX) of $5\times10^{-14}$ parts by volume, time constant six seconds; operating temperature, 200° C. maximum; and, ion source of pulsed or oscillatory corona-type or radioactive beta or alpha source such as Americium-241.

Figure 5:
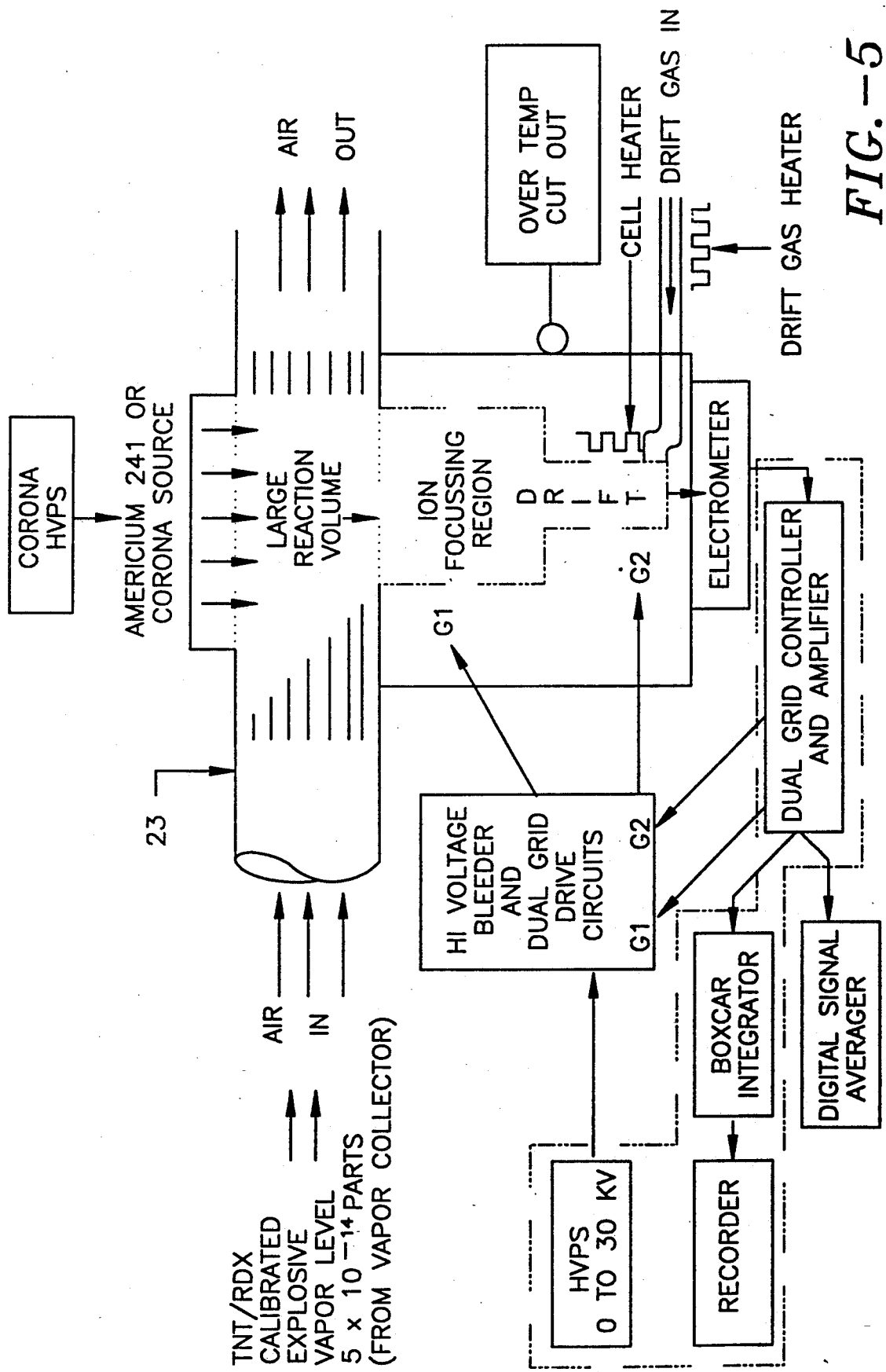
FIG. 5 is a schematic diagram showing the large reaction volume ion mobility spectrometer (LRVIMS) employed in the present invention.

The diagram of FIG. 5 shows the basic components of the LRVIMS instrument, which are discussed in greater detail hereinafter.

As is known to the art, the Ion Mobility Spectrometer (IMS) is an instrument for chemical analysis which identifies and quantifies the chemical being screened, such as an explosive or contaminant, in the vapor state at atmospheric pressure, based on time-of-flight of the ions of intent across a given region, the ion drift space. The IMS sensor structure contains an ionization source, ion-molecule reaction region and ion drift region.

Applicants have determined that a standard vapor signal of TNT and RDX in an air flow of up to 30 cubic feet per minute at a concentration of $5\times10^{-13}$ volume parts (molecules of TNT or RDX per molecule of air) will produce a signal-to-noise ratio of better than 2 to 1 with a six second time constant.

The commercially available Model LRV-1 sensor of PCP, Inc., West Palm Beach, Florida, has an Americium-241 source-an alpha particle emitter of 1.5 millicuries. The ionization range of the alpha prticle is short, less than ½ inch in air at atmosphperic pressure. The initial ionization components consist of positive ions and electrons which quickly attach to the oxygen and other electro-negative molecules in the air, including the target vapors, to form negative ions which are separated by the presence of an electric field. The polarity of the electric field moves the negative ions through the sample air flow (the ion-molecule reaction region or large reaction volume) towards the shutter grid and ion drift region. The objective in the ion-molecule reaction region is to convert the maximum possible number of reactant ions to negative explosive vapor ions and then cause the desired explosive vapor ions to enter the drift region. At the threshold signal level, less than one percent (1%) of the neutral TNT molecules are converted to negative ions.

As an important objective of the invention, the sensor of the new LRVIMS is improved to increase conversion efficiency and obtain the better, lower threshold signal at $5\times10^{-14}$ parts, which would be an improvement in signal-to-noise ratio by a factor of ten in comparison with the characteristics of the Model LRV-1. Areas of signal improvement are achieved by:

(1) Increasing the ion current by using a pulsed corona source (a factor of as much as 10 may be achieved in this manner);
(2) Increasing the ion-drift region area by a factor of four;
(3) Using ion focusing to focus ions into the ion-drift region (a factor of approximately four or more is achievable in this manner); and,
(4) Increasing ion drift voltage (increasing current approximately by a factor of two).

System Process Controllers

A computer or microprocessor 24 such as the IBM PC/AT or its equivalent is employed with available plug-in boards to control the variable apparatus in the system. The total system control, data processing signal analysis, and alarm circuit may be operated through one or more of such microprocessors.

As set forth hereinabove, the basic elements of the checked baggage screening system include the IMS sensor 23, the baggage examination module 20, the vapor collector 31 and associated plumbing, electrical control circuitry, and utilities. The closely related carry-on baggage/passenger screening includes a screening portal 21 which is substituted for the baggage module 20 as will be understood from the foregoing introduction and the following further detailed description of the invention.

Baggage Examiner (Explosive Vapor Signals From Baggage)

The fundamental problem solved by the invention is the obtaining of a vapor sample from the screened bag which may be reliably analyzed. The vapor concentration expected from an explosive material in a checked package/bag is estimated, in accordance with the invention, on the basis of the following working criteria:

(1) The explosive vapor within the container has reached vapor pressure equilibrium throughout the volume and contents of the container;

(2) When a partial vacuum is applied to the bag, there will be sufficient time and/or cracks/leakage to permit the passage of the explosive vapor-saturated air outward through the bag walls until the pressure inside and outside the package/bag are substantially equal. This occurs within seconds.

(3) The fractional vapor pressure of the explosive is $f_e$, the volume of the bag is $V_b$, and the bag is changed in effective volume by $AV_b$ by a suitable mechanism. The amount of explosive vapor that comes out of the bag is proportional to $f_e A V_b$ within a few seconds.

(4) This vapor may be diluted into a volume, V, which is the container volume, $V_c$, less the bag volume, i.e., $V = V_c - V_b$. Thus, the effective fractional vapor pressure becomes proportional to $f_e V_b / V$. This vapor may be continuously collected by the vapor collector with the rapid transport of the circulating gas flow.

With the circulating flow at 60 cubic feet per minute and with $(V_c - V_b)$ reduced to three cubic feet, the vapor is continuously collected. Approximately fifty percent (50%) of the available vapor exterior to the bag is collected during each pass of the gas through the collector, thus three cubic feet pass through the collector in three seconds. If the pressure inside and outside the bag is equalized quickly (compared to three seconds), then the bag can be re-pressurized and more vapor removed from the bag by continued vacuum/pressure oscillations.

If pressurization occurs in three seconds to ten percent (10%) above atmospheric pressure, and the explosive vapor mixes in the bag, twice as much air can be moved out on the next vacuum cycle. With five oscillations of pressure/vacuum per bag, the total explosive vapor amount that is available to the collector becomes proportional to $10 f_e (V_c - V_b)$. If $V_c = 10 \times V_b$, approximately the volume of the interior of the bag has been moved outside the bag, according to this approximate calculation, which assumes perfect mixing. In effect, the concentration is increased by a factor which equals the number of pumping cycles.

Advantageously, and in accordance with the invention, the vapor collector offers the advantage of decoupling the sensor from the vapor extractor cycle, which requires pressure/vacuum oscillations. Moreover, the vapor collector 31, by removing the explosive vapor from the air, causes "cleaner" air to be pumped into the bag during the pressure portion of the cycle. It is to be noted that the oscillatory motion of the piston wall is produced by a separate air flow.

A selected bag examination rate of B units per minute is achieved by the use of an automatic baggage handling module array. The baggage module array consists of a number N of baggage examination modules. Into each module, one or more bags are placed. The total examination cycle period is C seconds (e.g., sixty seconds). The time t required for baggage explosive signal sensing is determined by sensor response characteristics to obtain the proper positive signal response with a minimum number of false positives (false alarms) or false negatives (failure to produce a positive response with explosives present). This period is taken as six seconds. The total baggage examination cycle, of which this six second period is a part, is much longer to allow loading/unloading time, adequate time for causing the extraction of the explosive vapor from the bag, and transporting time to the sensor. Typically, the baggage examination cycle period is sixty seconds and is broken down as follows:

Loading 6 seconds
Vapor collection 42 seconds
Sensing 6 seconds
Unloading 6 seconds There are ten bags in the baggage module array, with one bag entering every six seconds and one bag leaving every six seconds.

The baggage/cargo package containing the explosive material is assumed to contain a volume which has reached an equilibrium saturation vapor pressure of the explosive. For forty-two seconds the bag is exposed to an oscillatory pressure/vacuum cycle of up to $\pm 0.2$ atmospheres. This treatment moves the explosive vapor from the bag to the chamber outside the bag. The module and vapor collector are sealed together as an air circulation unit during this period. The explosive vapor is moved from the module by the circulation of $\geq 60$ cubic feet/minute through the module and the dedicated vapor collector. Near the end of this collection cycle, the modules and vapor collector are physically separated by closing valves. Then the vapor collector is heated and the explosive vapor is volatilized. Ducts to the sensor are then opened and the explosive vapor flows through the sensor detection.

With this type of operation, when B bags are examined per minute and N bags are in the examination mode, $C/N = 60/B$ seconds are available during which the sensor can measure the vapor signal and reach a decision. If most of the examination time, C, is used to extract the vapor from the bag, then the available signal for the sensor is enhanced.

A typical large bag is approximately $2 \times 2 \frac{1}{2} \times 1$ or about five cubic feet. When the lower chamber volume is reduced to about ten cubic feet before applying the vacuum, one cubic foot of air must be removed from the upper chamber (above the piston) to reduce the pressure adjacent and within the bag to 0.9 atmospheres. Air, carrying the target vapors, will exit the bag to reach equilibrium at 0.9 atmospheres inside the bag. For a cycle of five oscillations per bag and for ten bags, a vacuum pump of fifty cubic feet per minute capacity is required. The requirement for compressed air was determined by assuming that the piston compartment is released to the atmosphere and then pressurized to 0.1 atmosphere (1.5 psig). The pressure is then released to atmospheric pressure of 0 psig. This process is repeated five times per bag. Thus, five cubic feet of free air is needed per bag per minute or fifty cubic feet for ten bags per minute.

The pressure/vacuum requirement for ten bags per minute and five oscillations of pressure/vacuum is achieved by the use of a suitable vacuum/pressure pump. A single compressor of approximately 3 H.P. will move air at this flow rate from one tank which goes 3.5 psig below atmosphere to another tank at 3.5 psig above atmosphere. Each tank will hold about thirty gallons or approximately four cubic feet.

The tanks are equipped with relief valves, safety valves and cutoff valves, as known in the art. The vacuum and pressurizing air is maintained outside and separate from the baggage compartment and thus does not contaminate the module or vapor collector with oil, etc. The oscillatory motion will be appropriately paced to keep the noise level as low as possible.

The oscillatory motion is handled with available commercial capacitance-type manometers and appropriate circuitry to control the valves by compressed air. Standard capacitance proximity switches may be used to optimize the position of the piston.

Explosive vapor collectors or "concentrators" made up of an adsorber, desorber and vapor collector, are used in Electron Capture Detector explosive vapor detection systems to serve one or more of the following purposes:

(a) To increase the explosive vapor sample concentration as compared to the sample concentration available by direct sampling;
(b) Remove the explosive vapor from the air and discharge it into another gas required by the detector, e.g., argon;
(c) To remove vapor sample from a large gas flow and discharge it into a lower gas flow, thereby also concentrating the sample; and
(d) To increase the ratio of the explosive vapor sample to the other extraneous, interfering, cluttering chemicals.

The concentrators used in the invention are mechanical devices utilizing explosive vapor adsorption on a specialized solid surface where the adsorption-desorption cycle takes place with temperature cycling. The physical location of each part of the cycle may be moved with a rotary or oscillatory motion. Other forms of concentrators, utilizing flowing powders or liquid sheets, may also be used in the practice of the invention.

In the explosive vapor detection system of the present invention, a stationary collector 31 is used with air flow control valves 40, 41 being employed to change the gas flow functionality during the vapor collection (adsorption) phase and the vapor evolution (desorption) phase.

The purpose of the vapor collector (concentrator) in the new detection system is to collect (adsorb) the explosive vapor from the module as it comes from the baggage during the vapor extraction part of the bag examination cycle and then quickly release (desorb, evolve) it prior to the transport to and measurement by the sensor.

It is known that pertinent parameters of vapor collector designs include temperature of adsorption, temperature of desorption, adsorption efficiency per unit area per unit flow, total area, flow impedance, air flow, adsorption time, desorption time, and overall efficiency.

Figure 7:
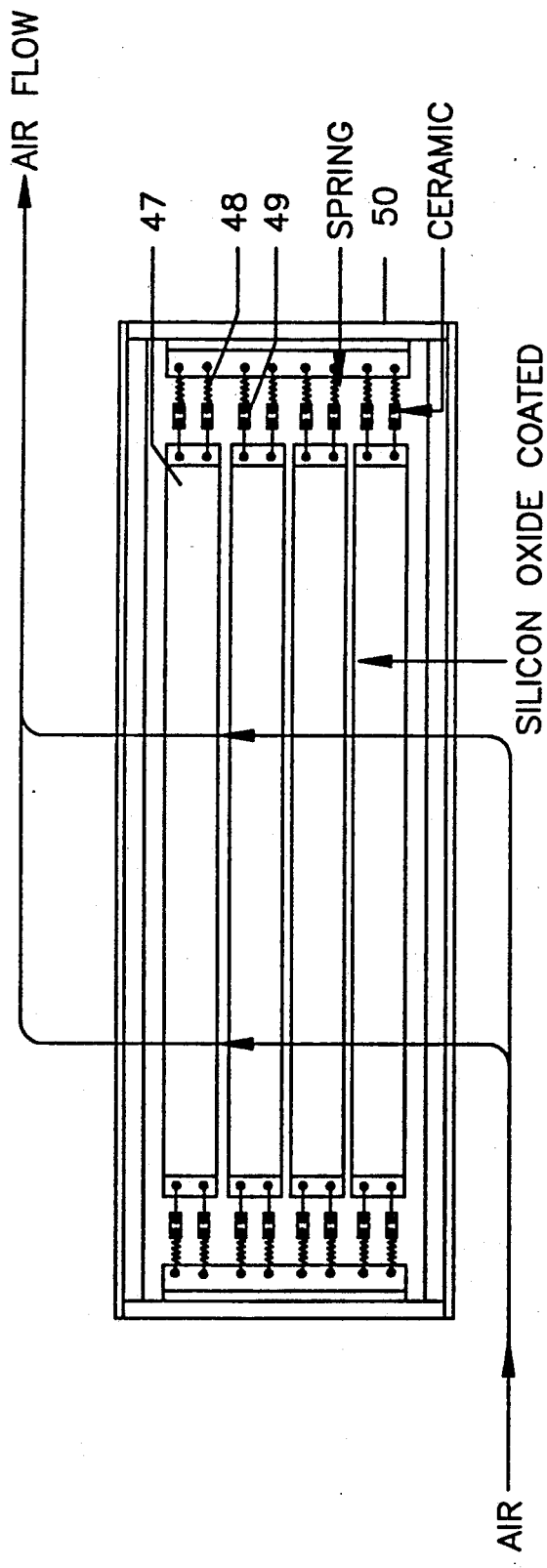
FIG. 7 is a top plan view of a vapor collector embodying the principles of the invention.
Figure 8:
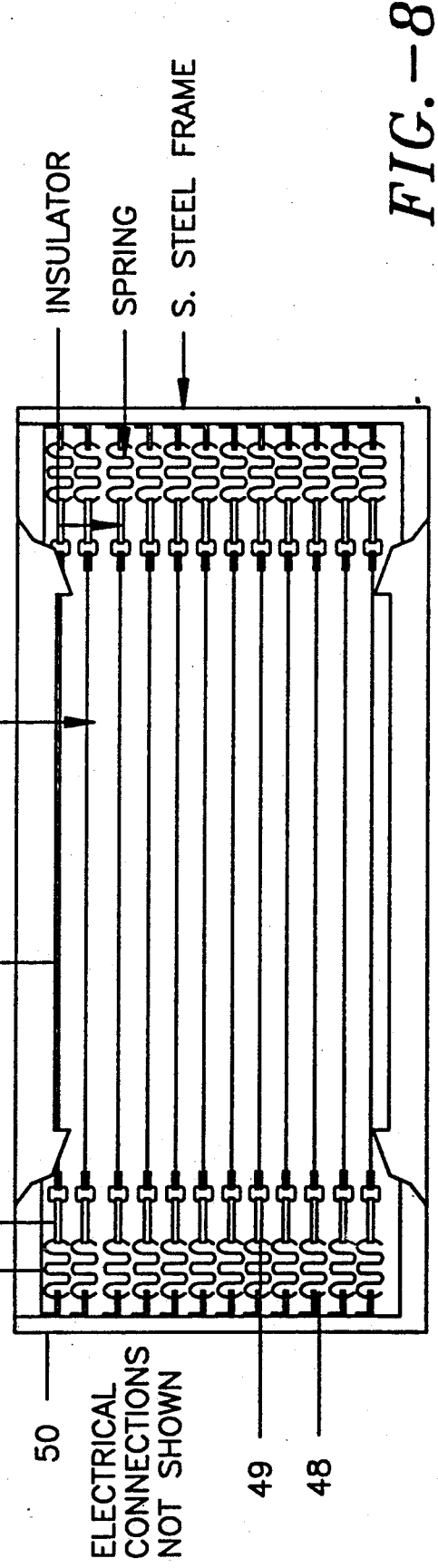
FIG. 8 is a side view of the vapor collector of FIG. 7.
Figure 9:
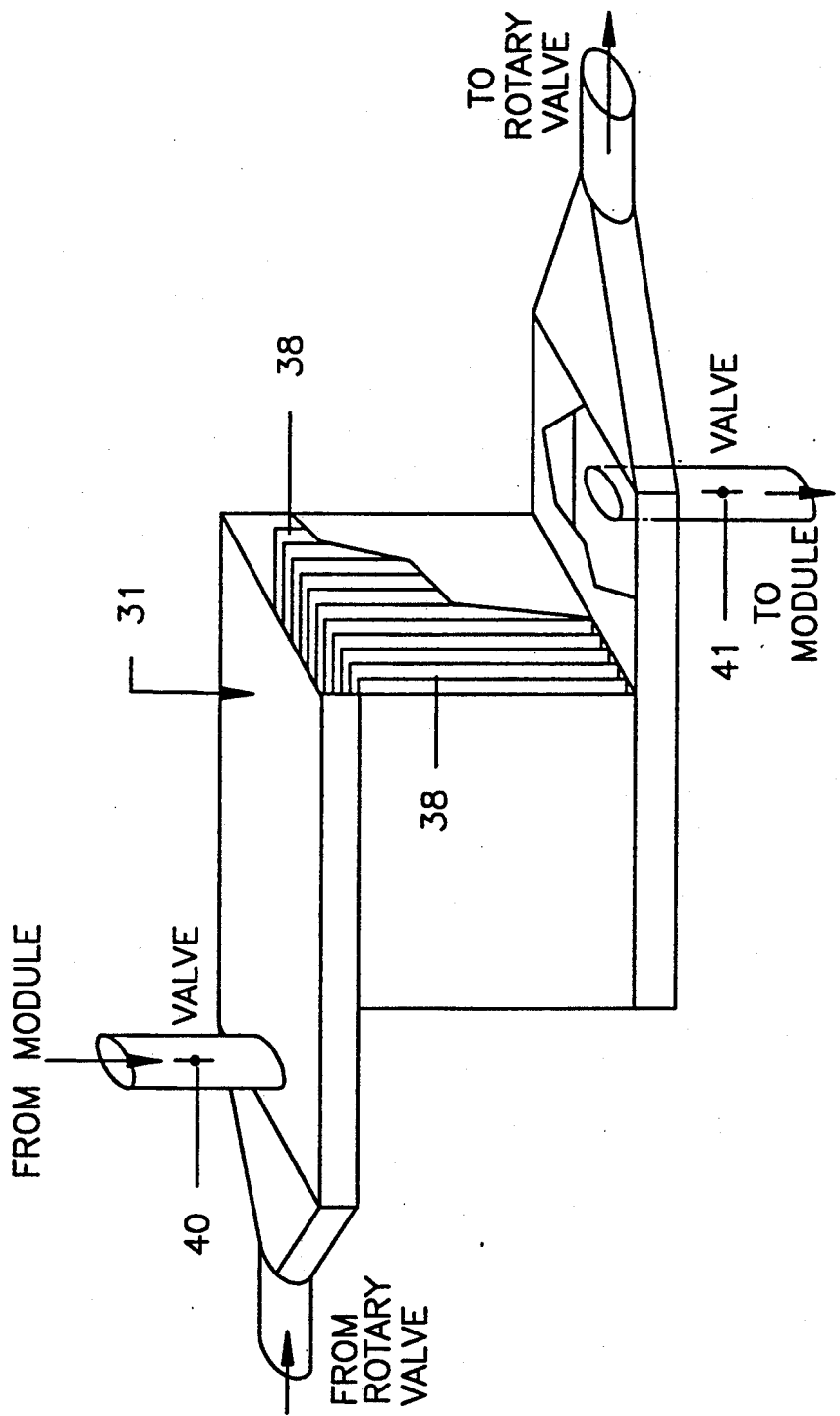
FIG. 9 is a perspective schematic diagram showing the housing for the vapor collector.

In the new apparatus, and as shown in FIGS. 7-9, thin silicon dioxide coated (0.002 inches thick) on wide (10 cm) nichrome ribbons 47 are employed as an effective adsorber surface. The ribbons have low thermal capacity so that they can be heated rapidly and cooled efficiently and quickly. An effective configuration of multiple layers, preferably 20 in number, each 10 cm by 30 cm in area, is employed. Each layer or "sheet" is separate and constructed of four ribbons, each 0.002 inches thick, one inch wide, and one foot long. Each ribbon is spring-loaded, bridle-style, with a small spring 48 and insulator 49 at each end. The individual layers are mounted five millimeters apart in a stainless enclosure 50.

The design of the vapor collector 31 is based on data which shows that explosive vapors adhere to silica ($SiO_2$) surfaces 47 efficiently at temperatures below 80° C. and are given off readily above 150° C. From the measured performance observed by others using this technology, it is believed that an explosive molecule striking the surface has close to 100% probability of sticking. With this as a basis and with the use of the gas diffusion equations, the performance of the vapor collector 31 for the baggage examination module 20 may be reliably estimated.

A set of twenty parallel plates arrayed in the manner shown in FIGS. 7 and 8 has an area of 10 cm by 30 cm and enclose a volume of 10 cm×10 cm or, 3,000 cubic centimeters.

During the vacuum/pressure oscillation of the module of ±10%, and at the increased temperature of a few percent in the actual vapor collector, a value of about $D=0.09$ cm$^2$/sec is obtained. The average time for the molecule to reach the duct wall is given by the relationship $t=[Dn^2 (1/w^2+1/d^2)]^{-1}=d^2/D/n^2$; $t=1/n^2 \cdot (0.5)^2 cm^2/0.9\ cm^2/sec=0.28$ sec. In this time t, one-half of the vapor molecules reach the wall and, assuming 100% sticking probability, will adhere.

The flow rate F to give a 0.28 seconds residence time in the vapor collection duct is given by $F=V$ (cm$^3$)/t (sec)=(4 cm×30 cm/0.28 sec) 60 sec/min=1700 liters/minute=60 cubic feet/minute. Thus, at this circulating air flow rate, 50% of the explosive molecules are removed from 60 cubic feet of volume in one minute without recirculation. The gas is discharged and not returned again to the collector in this case. When recirculation is used, as for example thirty cubic feet circulated twice or twenty cubic feet is circulated three times, fifty percent (50%) of the exiting vapor in the gas phase is removed with each pass. Thus, the thirty cubic feet has only twenty-five percent (25%) of the explosive vapor molecules remaining after one minute. If twenty cubic feet are used, then 12.5% remains after one minute in the gas phase. This recirculation feature is important since a small volume of gas from the module is circulated several times at sixty cubic feet/minute in this example.

The number of circulation passes depends on the net volume in the module between the bag and the case. Obviously, one hundred percent (100%) absorption is approached with this argument if the module and bag wall do not absorb the explosive vapor. Since such is not the case, bag and module wall absorption places a limit below one hundred percent (100%).

An increase in vapor collection plates, spaced closer, will increase the collection efficiency per unit time. It is important to recognize that the spacing d of the plates caused the efficiency to increase by $d^2$ as d is decreased.

In addition, multiple collectors, arranged in cascade as shown in FIG. 19, can be used. First collector unit 31 has its array of collector plates 38, after the absorption cycle is completed valve 43′ operates, and the collected molecules are desorbed and transferred by blower 51 into collector 31′. The dimensions of collector 31′ is chosen to provide a smaller volume than that of the first collector 31. After absorption is completed valve 44 opens to transfer the subsequent desorbed molecules to the sensor. As IMS sensors are vapor-concentration sensitive, the collection of the molecules onto collector plates within successively smaller collector volumes increases the concentration of material in the gas phase and results in a better signal-to-noise ratio in the detector. the collector can be cascaded in continuing sequence as may be required or desired. Additional piping 52', along with appropriate timing circuitry (not shown) may be required to direct the transfer air flow between the collectors for molecule transfer.

A simple model of the module, bag, and vapor collector was used to estimate the distribution of the explosive vapor after thirty seconds of circulation of sixty cubic feet/minute in a single stage configuration.

Considering the vapor collector described, using a 15.6 cubic foot module (2.5'×2.5'×2.5') with a large package that fits within two inches of the walls of the module, the package volume is 12.7 cubic feet (2.33'×2.33'×2.33') and the difference is 2.9 cubic feet. This volume difference is considered to be the equivalent of a duct with a wall spacing of five cm.

From the diffusion equation (1) $t=[D^2 (1/W^2+1/d^2)]^{-1}=d^2 D^2$, the average time for a molecule to reach the wall was compared to residence time in a vapor collector with a wall spacing of 0.5 cm. This time, 28 seconds $[(5\text{ cm}/0.5\text{ cm})^2\times 0.28\text{ sec}]$, is one hundred times longer than the residence time in the vapor collector.

With each pass of the air through the vapor collector in 0.28 seconds at sixty cubic feet/minute, fifty percent (50%) of the vapor adheres to the surface. Each pass through the net volume of 2.9 cubic feet at sixty cubic feet/minute takes about three seconds, with an estimated five percent (5%) adsorption, since the average time for fifty percent (50%) collection is twenty-eight seconds. In this simple model, the wall spacing is the dominant variable.

This ratio of fifty percent (50%) to five percent (5%) holds for every circulation pass and the vapor collector would achieve ninety percent (90%) collection of the available vapor. Even if the wall were made of low adsorption material, the potential improvement is only ten percent (10%). An increase of the spacing between the wall and the bag to ten cm decreases the wall loss in this model and achieves 99% efficiency. This model is overly simplified. Most of the vapor absorption loss will occur in the baggage closures where spacings are much closer.

As a result of diffusion equations and adhering of the explosive vapor to tube walls, differences in pipe diameters used in the air flow plumbing are not critical to the system design. This is the case where the diameter is one inch or larger at ambient temperature. This circumstance arises from the fact that a high flow velocity is used, but well below the turbulence level, in a smooth pipe, and the available diffusion time is very small.

The flow impedance of the pipe becomes important as diameters get too small, for example, less than one-half inch, because it is desired to have multi-cubic feet per minute flows with reasonable fractional horsepower blowers. The use of one inch diameter pipe is practical as a compromise, with a resultant saving in plumbing, valves and associated costs.

Vapor loss to a wall is dependent on a diffusion time, $t_p$ for the streamline gas flow given by the equation $$t_D=[D\pi^2 (1/w^2+1/d^2)]^{-1}=d^2/D\pi^2,$$

where $t_D$ is proportional to $r^2/D$. The smaller the value of the pipe radius, r, the more likely an explosive vapor molecule will reach the wall and stick.

The power requirements and heating time for vapor desorption are pertinent parameters of the vapor collector embodiment of the present invention. These are determined for the apparatus built from the multi-layer configuration of nichrome heater ribbon, as follows:

The device sensor consists of twenty layers of nichrome sheet ten cm wide by thirty cm long, spaced 0.5 cm apart, forming a duct approximately ten cm x thirty cm in cross-sectional area. Each nichrome sheet is 0.001 inches thick and has a specific resistance of 106 micro ohm/cm²/ Each square of this foil of any dimension and 0.001" thick, e.g., 10 cm×10 cm×0.001" thick, has a - resistance of 0.042 ohms. The specific heat of nichrome is 0.11 calories/gram/degree Celsius, with a specific gravity of 8.0 grams/cubic centimeter. For a temperature rise of about 200° C., the amount of heat in watt-seconds required per layer is calculated as follows:

Q(watt-seconds)=0.11 calories /gm° C.×4.18 watt-sec/cal×300 cm²×0.001 inches×2.5 cm/in×8 gm/cm³×200° C.=550 watt-seconds per layer.

For 20 layers $Q=1.1\times 10^4$ watt-seconds.

The resistance of the 20 nichrome layers is arranged as sixty squares of 10 cm×10 cm×0.001 inch material. A thinner material of 0.0005 inches thick is also available and would reduce heating requirements proportionally. The squares are wired to draw up to 25 amperes on 208 volts from a power pair of a three-phase, 60 Hz power (240 volts is also available). Therefore, the total available power is up to 5200 watts. Since $1.1\times 10^4$ watt-seconds is required to reach 200° C., the time required is about two seconds. A standard solid state power supply can provide this type of power pulse control.

The average power drawn from the line is smaller, since the power surge of 5200 watts is required for only two seconds. This power surge occurs only ten times per minute for the ten vapor collectors.

As previously disclosed, a longer heating time may also be used, in which case the explosive vaporization may be advanced ahead of the sample gas flow, after stopping the module circulation. A six second advance also reduces the power requirements proportionally.

The air flow through the vapor collector is reduced to 10 to 20 cubic feet/minute for vapor desorption. At fifteen cubic feet/minute flow the power required to maintain the 200° C. temperature is only about 1000 watts, which is maintained for six seconds by a solid state relay by cycling the power on and off. A separate fan 51 operates at fifteen cubic feet/minute during the vapor desorption (see FIGS. 2 and 3). The vapor is discharged into the sensor as previously described.

After six seconds of sample collection, rapid cooling of the collector is required. With a module airstream, at sixty cubic feet/minute, the rate of cooling initially is about at a 4000 watt rate, where the heat stored is approximately 11,000 watt-seconds. Since the temperature drop is exponential, the time to reach a temperature below 80° C. is about six seconds (i.e., as short as the baggage loading cycle). The heat is transferred into the module as well as outside, as the module doors are opened to load/unload the bag from the module. The heat may also be used in part to heat the walls of the module to reduce vapor adsorption. Thus, the vapor collector is prepared for recycling by the time the next bag is loaded into the module.

The preferred format for the operation of multiple modules is with an array of vapor collectors, separated from the baggage examination modules. One vapor collector is dedicated to operate with one module, but all the vapor collectors closely adjoin the sensor, rather than being located in or adjacent to each module (See FIG. 2).

This geometry offers several system advantages. One is that the vapor-collector sensor-to-plumbing is short, and particulate-free filtered air can be readily supplied to carry the explosive vapor to the sensor with a 10 cubic feet/minute blower. The disadvantage of longer plumbing between the module and the vapor collector does not add significantly to vapor loss at a 60 cubic feet/minute circulation flow as compared to the loss in the module itself. Another advantage is that several sizes of modules may be mixed in a multi-module arrangement, as needed, to handle larger sized or odd shaped packages. Two inch diameter pipes are highly suitable for connection, although in some cases, even one inch diameter pipes may be used.

Figure 10:
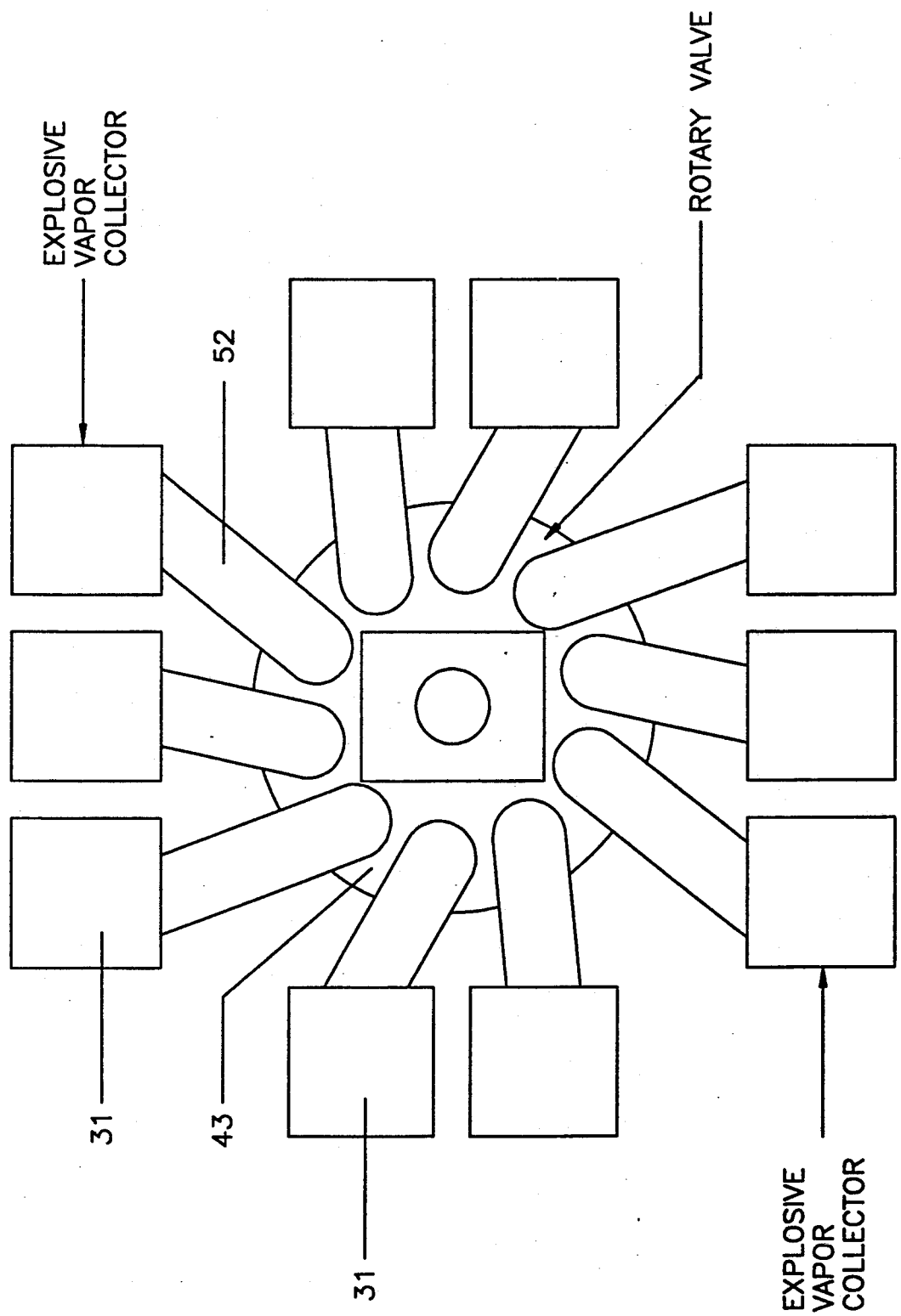
FIG. 10 is a schematic diagram showing an array of ten explosive vapor collectors and a rotary valve coupler therefor.

For signal generation, filtered air is blown through a specially designed rotary valve 43 with two inch ports 52 into each vapor collector 31 in turn, as seen in FIGS. 3 and 10. A similar synchronized rotary valve 44 at the exit of the collector 31, transports the evolved vapor to the sensor 23. Each port is open for six seconds every minute for the ten unit array. Valves 40, 41 (FIG. 3) to and from each module control the sixty cubic feet/minute flow circulating through the module to carry the vapor to the collector 31. These valves are closed prior to the rotary valves opening by a lead time of three seconds. Heat is applied to the vapor collector to raise its temperature of 200° C. in less than one second. Thus, the vapor is in the gas phase when the sensor channel is opened and the ten cubic feet/minute flow carries the vapor a short distance to the sensor 23 in less than 0.3 seconds. To avoid cross contamination in the common collection plenum of the rotary valve, each of the ten ports is piped to the common sensor port by the use of separate pipes 53. These pipes are designed to flow smoothly into the entrance plenum of the sensor.

Figure 11:
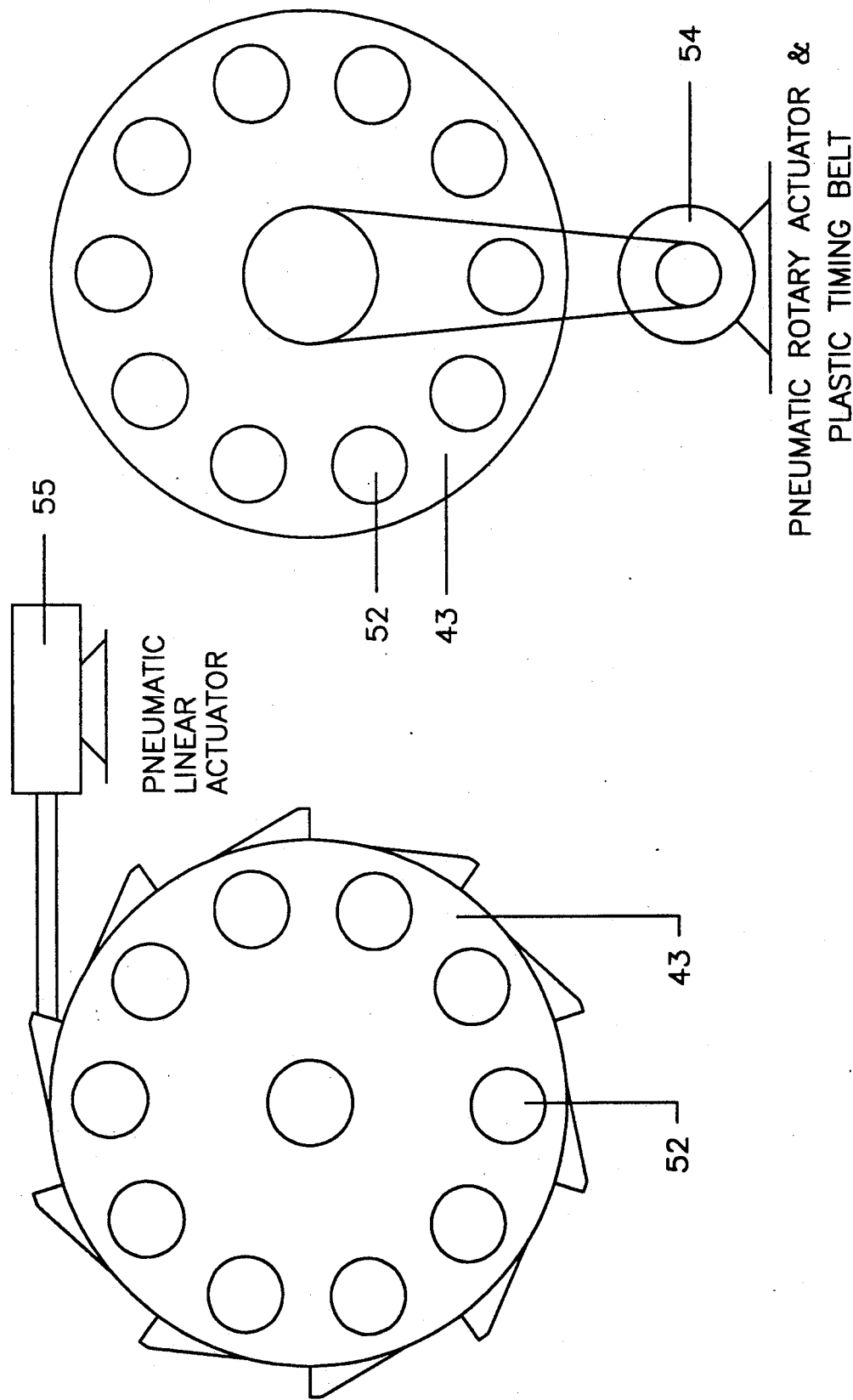
FIGS. 11A and 11B depict the actuation by pneumatic linear actuator and rotary actuator, respectively, of the ports of the rotary valve of FIG. 10.

The valves for air flow control are standard commercial rotary or flapper valves made of Teflon. The rotary valve (see FIG. 11) is turned and indexed 36° by a pneumatic linear actuator 55 or by a stepped pneumatic rotary actuator 54 which is coupled, by a standard timing belt, to the valve. The standard rotary actuators move arcuately 90° on each movement; timing belt gearing moves the valve rotor 36°, i.e., ten steps per revolution. A circular Teflon coated, stainless steel plate, with a single two inch opening, may be used to rotate between two fixed Teflon coated plates. This sandwich is spring loaded to exert a bearing pressure to minimize leakage. The fixed plate has ten 2 inch holes and is permanently connected to an entrance manifold to which the pipes 52 connect. The other fixed plate may have a similar arrangement opening to a segmented exit manifold. The collectors may be placed in a cascade arrangement to concentrate the vapors, generating a better signal-to-noise ratio in the detector. In such an arrangement, material adsorbed in a vapor collector of volume can be desorbed into a smaller volume collector where the vapors are again adsorbed. This places the total available mass of chemical material into succeedingly smaller volumes, providing an increased concentration of material in the ultimate gas phase.

The screening of passengers and carry-on baggage poses a different problem from that of screening checked baggage examination because of differences in enclosure module size. For example, a box, 3"×3"×7", e.g., a "telephone booth" enclosure, has 63 cubic feet and, with a flow of 120 cubic feet/minute, would clear about once in 0.5 minutes. This portal volume is on the small side for the comfort of a passenger being screened with one carry-on bag. A larger, practical size of 4"×4"×7", e.g., 100 cubic feet, is required.

To screen ten people per minute requires the examination of only the air that passes close to the person. The explosive vapor may thus be removed with curtain-type air flow. The curtain air flow layer is a few inches from the person and is most likely to contain the explosive vapor that is wafted, diffused, or convected from the clothing and/or carried-on bag. This air flow format suggests the use of a directed laminar air flow in the portal.

It has been determined that a vertical collection manifold, centered on an air curtain flowing at sixty cubic feet/minute, can detect TNT vapor from a small package on a mannequin in approximately six seconds. This small gas volume of six cubic feet, is useful, but a more efficient vapor collection is desirable.

To that end, vapor collection may be substantially improved by the use of a thirty second sampling time with five portals 21 operating in parallel (FIG. 1) with one sensor. Each portal has two stationary vapor collector assemblies dedicated to its use. One vapor collector collects explosive vapor while the other is heated to evolve its already collected vapor, as it is connected to the sensor and then cooled in preparation for reuse. The vapor from the collector is discharged from the sensor and measured in six seconds and cools for twenty-four seconds. It then collects vapor from the portal for about thirty seconds as the person enters, stands in the portal, and leaves.

During the vapor collection phase, a flow of about 120 cubic feet/minute is employed which is, in fact, a "breeze" of approximately two miles per hour, over an area of three feet wide by one foot. When a thirty second period of vapor collection is used at 120 cubic feet/minute, there is a gain of almost ten in signal as compared to a sixty cubic feet/minute flow and six second direct sampling.

The design of the portal vapor collector is the same as the one set forth above. Each vapor collector is fifty percent (50%) efficient, on a single pass at sixty cubic feet/minute. If pairs are used in parallel (or four total), the efficiency is still fifty percent (50%) at 120 cubic feet/minute overall. The net gain in signal is then five.

A further advantage of the vapor collector is the reduction in background chemical clutter noise that may be achieved by the selective collection of more explosive vapor and less background.

The provision of a new and improved Large Reaction Volume Ion Mobility Spectrometer (LRVIMS) as the sensor is one of the objectives of the present invention. Improvements in the LRVIMS sensor are also specific objectives of the present invention.

The new and improved LRVIMS consists of the following elements, shown in FIG. 5:

Corona ionization source (Americium-241 alpha source, 2 mCi)

Large Reaction Volume (20 cm ×20 cm×20 cm)

Ion Transition Region (ITR) with an ion shutter grid

Ion Focusing Region (IFR) based on conical geometry

Four standard Ion Drift Regions in parallel with improved insulation to operate at a higher voltage Associate electronic circuitry Readout(s)

The corona ion source is operated with current in the form of random series of pulses. The discharge operates as a relaxation oscillator. This oscillation is synchronized to give a pulse source which produces a burst of ionization in synchronism with the ion drift time. The corona discharge is off during the time the vapor signal is measured. Thus, no noise is generated directly by the corona source.

In accordance with the invention, alternate ways of driving the corona source include using a pulse transformer or audio frequency oscillation.

The ion-molecule reaction volume has been increased (in comparison to that in the LRV-1) to 20 cm×20 cm×20 cm or eight liters in volume. The sensor responds to concentration, i.e., the number of explosive vapor molecules present in the sensor. A better (lower) threshold signal is achieved by using larger reaction volume with a larger cross section in the direction of the air flow. An increase in volume influences other design parameters. The reaction region height is in the direction of the electric field and thus requires a greater voltage across the reaction region. An increase in width requires that the entrance aperture to the drift region also be increased; this is also true for an increase in the depth of the reaction region. The height of the reaction region is increased by a factor of two. The result of these changes is an increase in signal by a factor of eight.

An increase in signal current is achieved by using a larger applied voltage. Multiple parallel drift regions of the standard commercial type are used for this purpose. The applied voltage and field is increased by using larger insulating sapphire beads between the rings. The ion grids are of the standard type.

Noise is of equal importance with the signal in the performance of the IMS sensor. The noise frequency bandwidth is finally limited by the six second signal band, which is about zero to 1/6 cycles per second.

Noise in the measurement of a threshold signal arises from a number of sources:

The amplifier;

Mechanical vibration, such as air flow, motors, etc.;

Electrical noise, such as power line noise, thermostat cycling, etc.; and

Clutter from interfering chemical species.

The ion transition region (ITR) has the cross section of the reaction region and the same voltage gradient. The ITR is provided to separate the rapid air flow through the LRVIMS ion-molecule reaction region from the ion focusing region, in order to eliminate possible turbulent gas effects which may possibly disturb the ion focusing. This region may be approximately four cm deep. The ion focusing region may also serve as the ion transition region.

A first active ion control grid is placed in the transition region to reduce space charge effects due to the unreacted reactant ions.

Before the ion focusing takes place, the first ion control grid is pulsed to provide a sheet of ions of all mobilities which will enter the space between the final grid (grid 1) and the next ion control, the second grid (grid 2). Grid 2 is at the entrance to the standard ion drift region. In this grid 1 to grid 2 region, the ion focusing region (IFT), the faster reactant ions of the pulsed ion mixture proceed ahead of the slower TNT (or other explosive) ions. At the TNT threshold signal, the lower density TNT ions proceed more slowly, without the presence of the faster reactant ions, toward grid 2. Grid 2 is timed to open at the proper delay with respect to grid 1 so that the TNT ions enter the drift region, which is the grid 2 to collector region. The reactant ions which would have been present at grid 2 have been blocked by the closed grid 1. The reactant ions which enter the IFT with TNT ions have already been collected by the closed grid 2, which is timed to open only for the TNT ions. This method of tuning the chemical species is used to measure all the explosive species simultaneously.

The ion focusing region (IFR) concentrates the ion beam from the large area to a much smaller area, in order to pass all the ions into the ion drift region (IDR) for mobility measurement. In the disclosed example, the area is reduced from typically 20 cm×20 cm to 10 cm×10 cm or less, comprising four standard 5 cm diameter ion drift regions mounted and operating in parallel, to increase the effective diameter of the ion drift regions.

The focusing process is based on the principle that ions at atmospherical pressure will follow the electric lines of force in the absence of appreciable space charge repulsion. (Space charge repulsion produces a defocusing electric field of several volts per cm for an ion density of $10^7$ ions/cm$^3$). A density less than $10^7$ ions per cm$^3$ is certainly the case for a threshold signal in the absence of reactant ions.

The reaction region has a lateral surface area of 20 cm×20 cm, which is focused into a dimension of 10 cm×10 cm, i.e., the input area of the four ion drift regions operating in parallel. The equivalent spherical ion flow design is a conical section of a cone with a total included angle of 90°.

The spherically-formed field is determined by the set of flat disk electrodes. The electrodes are spaced ¼ cm apart, and there are twenty electrodes for the five cm spacing.

The remainder of the IMS may be a standard Phemto-Chem$_R$ 100 unit with an Ion Drift Region (IDR) of ten cm diameter and the screen grid and collector assembly. An ion beam of ten cm diameter, produced by the ion focusing region, will enter the enlarged ion drift region.

The source and large reaction volume IMS operate at the high potential and the ion collector is grounded. The total voltage across the cell is as follows, using an electric field E of 600 v/cm.

| Region | Distance × E | Voltage Difference |
|--------|--------------|--------------------|
| LRV | 20 × 600 volts/cm | 12,000 |
| ITR | 2 × 600 volts/cm | 1,200 |
| IFR | 5 × m (20 electrodes) | 8,500 |
| IDR | 10 × 600 volts/cm | 6,000 |

| -continued | | |
|---|---|---|
| Region | Distance × E | Voltage Difference |
| | TOTAL | 27,700 |

Thus, approximately 30,000 volts is an upper bound—similar to a large TV tube. For the new LRVIMS, there is 12,000 across the twenty cm ion-molecule reaction region, 1,200 volts across the ion transition region, 8,500 volts across the ion focusing region, and 6,000 volts across the ion drift region. These fields are larger, by a factor of two, when compared with the aforementioned Model LRV-1 IMS.

Exemplary Airport Screening System

Figure 12:
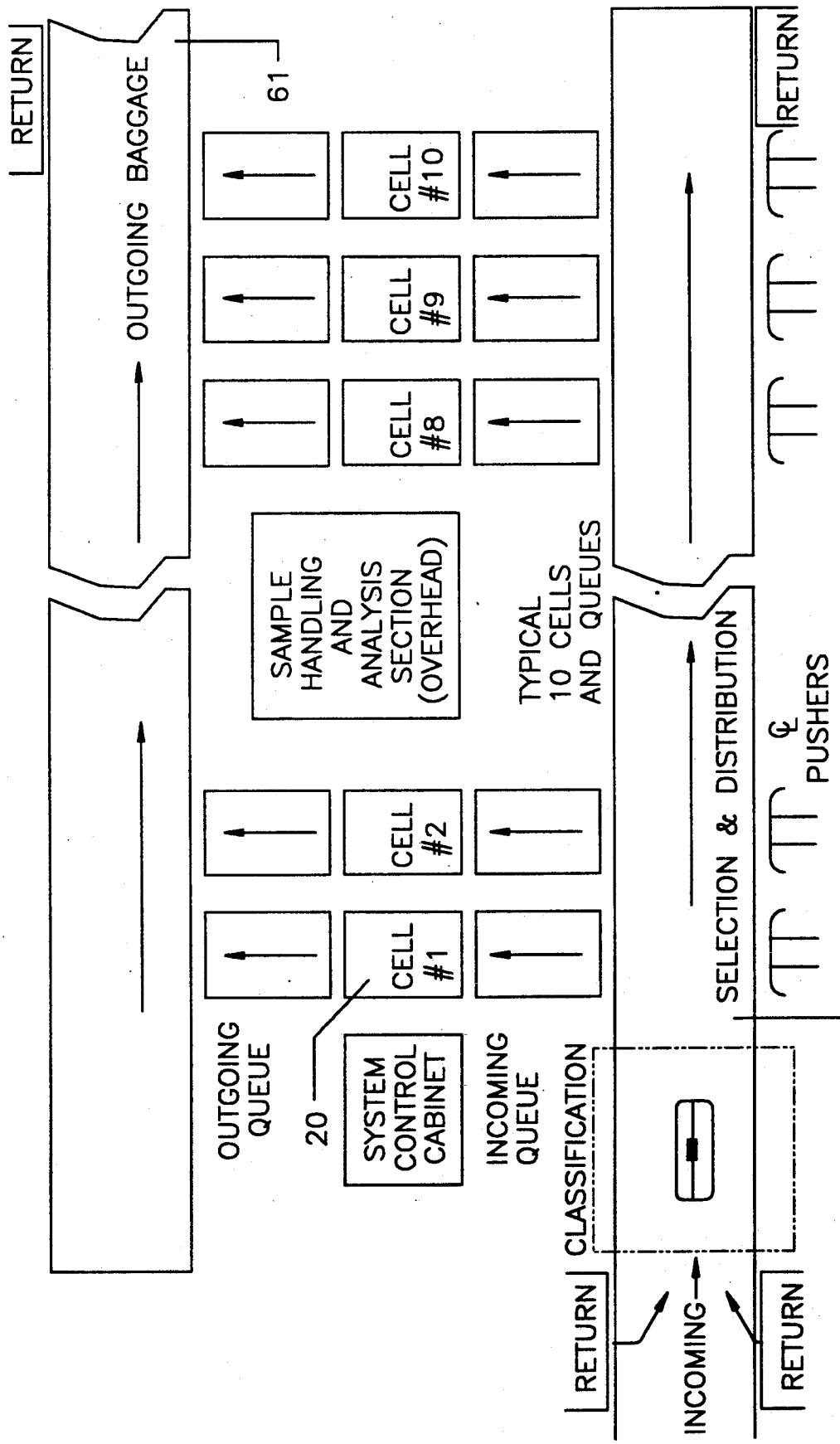
FIG. 12 is an exemplary baggage examination system designed in accordance with the invention.
Figure 13:
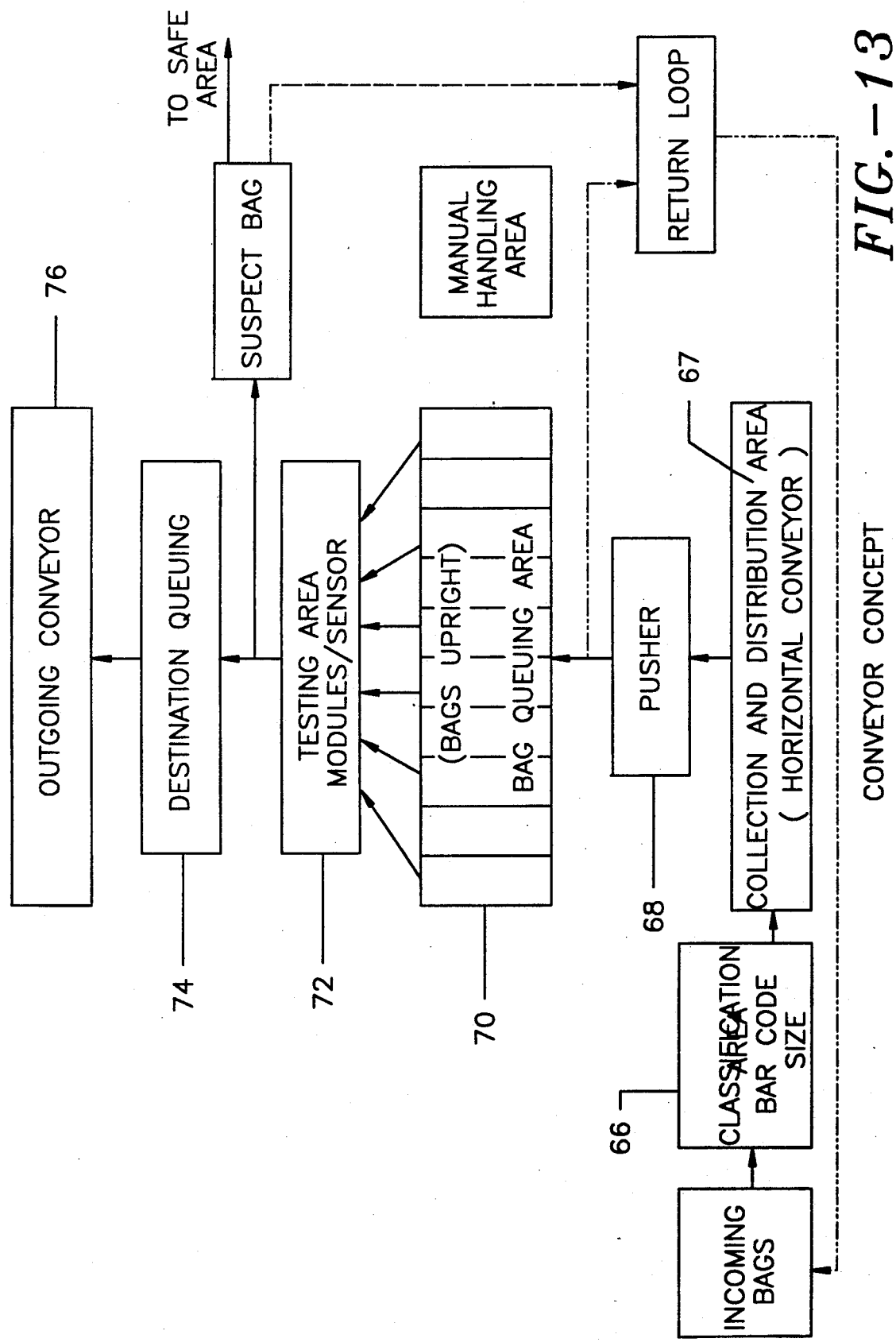
FIG. 13 is a block diagram illustrating a conveyer concept of baggage screening.
Figure 14:
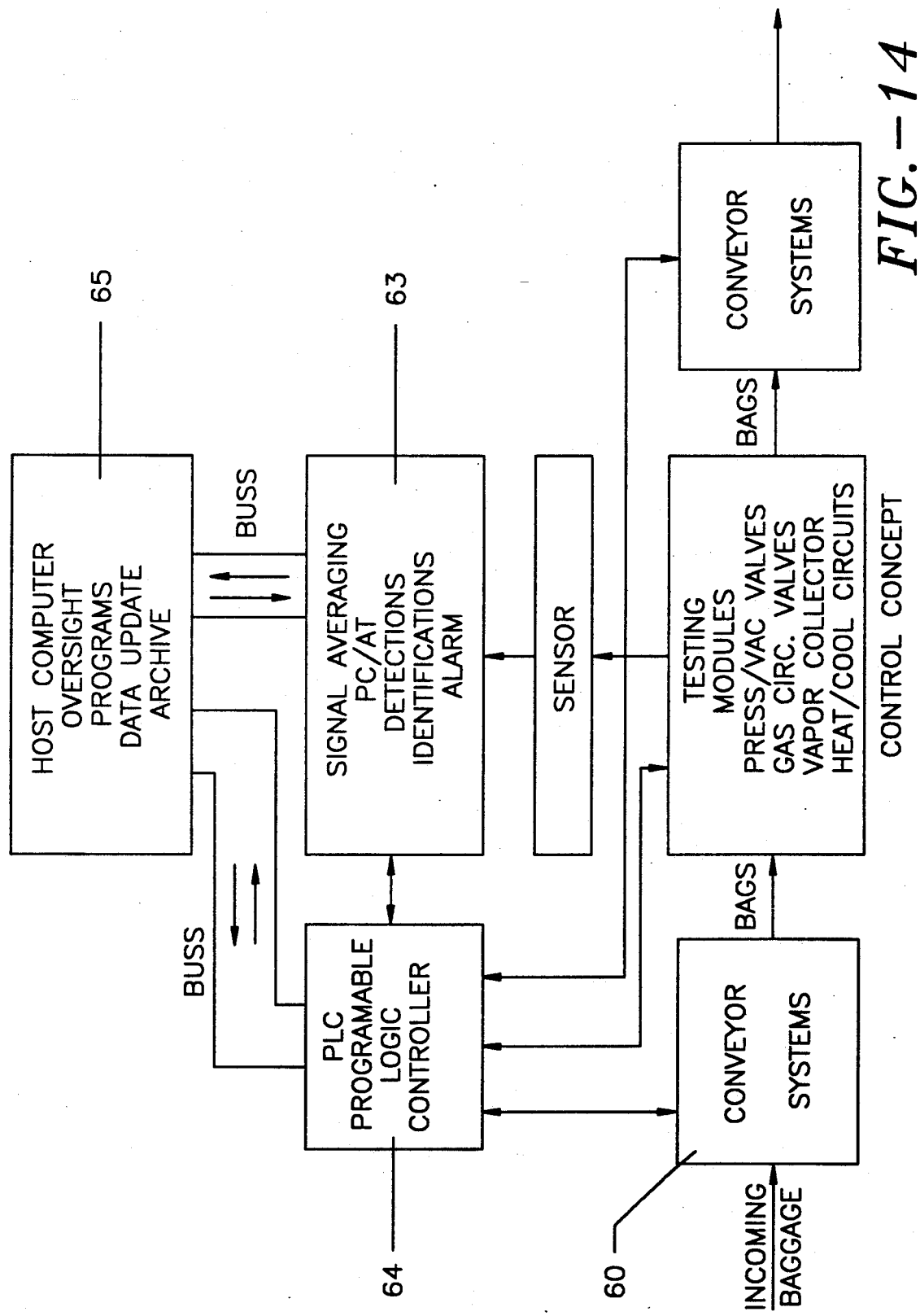
FIG. 14 is a block diagram illustrating the control system for the baggage screening systems of FIGS. 12 and 13.

An exemplary overall system embodying the invention is shown diagrammatically in FIGS. 12 to 14. An incoming conveyo system 60 routes the incoming baggage to one of the ten Explosive Vapor Detection Modules 20 and, if no vapors are detected, the baggage continues onward to an outgoing conveyor 61 to the baggage cart loading area for forwarding to the aircraft. The conveyor operation is automatic and includes features such as baggage sizing, destination determination, baggage tracking through the system, retest for bags showing questionable detections, and automatic routing to a safe area for bags showing unquestioned detection of an explosive or contraband substance.

Three computers 63, 64, 65 (FIG. 14) are employed to control the system shown in FIGS. 12 and 13. A detection computer 63 works with the Ion Mobility Spectrometer (IMS) signal and provides signal averaging to improve the signal-to-noise ratio, to detect and to quantitate explosive vapors, and to initiate an alarm in their presence. A Programmable Logic Controller (PLC) 64 handles the real time control of the conveyor/detection modules, using redundant, state-of-the-art equipment. A third computer 65 acts as the host computer and interfaces the system to the supervisory personnel, maintains records, prepares reports, updates the system with necessary data, alarms when detections or faults occur, and supervises the full system.

The IMS explosive vapor detector with its high sensitivity to explosive vapors is, of course, a central and critical component of the overall system. Accordingly, for redundancy and on-line maintenance to insure that the whole purpose of the system is not defeated by an occasional or random failure, the exemplary system may include two full IMS vapor detection systems with a series gas connection between the sensors and full parallel redundancy. In this situation, true explosive vapor detection must occur in both systems simultaneously, thereby reducing any false alarm rate. In case of failure of either IMS system, the other IMS is fully handling the overall system while repairs are made.

The most likely failure mode, historically, has been slowly increasing contamination of the IMS cell over a period of six to nine months. Therefore, a third IMS cell is installed in a "clean-up fixture". This additional IMS cell is maintained about 50° C. hotter than the operating cells while clean, filtered air is circulated through it. IMS cells can then be routinely interchanged between the operating and clean-up positions, on a monthly basis, to prevent or forestall this failure mode.

The IMS sensor computer 63 may be an environmentally ruggedized industrial process version of the IBM-/AT computer, such as that manufactured by IBM for Allen-Bradley (Allen-Bradley Model 6122). It contains a special signal averaging front end board and a specific program to handle the detector signal from the IMS sensor and determine the presence of the explosive vapors and their signal strength based on ion mobility. This information is transferred to the host computer 65 and to the PLC 64 for appropriate action.

The programmable logic controller (PLC) system 64 reads and controls all bar code scanners, photo-electric sensors, encoders, conveyors, baggage pushers, doors, cyclic vacuum/pressure actions, valving between the baggage modules and their vapor collectors and the sensor.

The PLC is of the fault tolerant or double redundant type containing four to five 16-bit coprocessors. These units provide high rates of scan/execution time. The PLC provides the necessary computational power of real time, floating point math to track a bag, using Boolean algebra and ladder logic. The units are hardened for the environment. They are resistant to electro-magnetic interference (EMI), radio frequency interference (RFI), electro-static discharge (ESD), power line surges, shock, vibration, and temperature and humidity extremes. The redundant PLCs can operate at high speeds (10 MHz), provide fault indication at the unit and at the host computer, and feature "hot" replacement by a technician of faulty modules, while the system remains fully operational. Battery back-up is available in the event of power failure.

Initially, the raw data relating to baggage size, position and, optimally, destination, is routed to the PLC 64. With reference to FIG. 13, the PLC senses the baggage size, calculates the volume, selects the size of the inspection module to be used, combines this data with the resident information on the current queuing profile, makes the necessary queuing decisions and initiates the proper commands to the system for further action, allowing maximum time utilization of the sensing modules.

Baggage tracking within the PLC is accomplished by a master shift register (MSR) subroutine, which models the entire system with its series/parallel paths. Following sizing of each bag/parcel in the classification area 66, the MSR is indexed by the movements of conveyor 67 through the pulse encoders, augmented by the additional photo cells at the start of each conveyor.

Each centerline pusher 68 is activated in the appropriate time interval, based on the baggage tracking and queuing decisions made by the PLC, with photo cell input from the pusher. The bags are then queued for testing in area 70.

Each explosive vapor inspection module in testing area 72 is controlled by a drum timer subroutine within the PLC, initiated at the appropriate instant by the MSR subroutine and synchronized with each of the other modules. Thereafter, this one minute time dependent program controls all of the valves and heat cycles of the module and associated vapor collector.

Each six seconds, at the completion of the explosive vapor detection phase of the cycle, the sensor computer result concerning the explosive vapors detected (absence of/presence of/strength of) is sent to the PLC where the baggage routing decisions are made. With no signals or strong signals, the baggage is removed from the vapor detection module and is routed for aircraft loading through queue 74 and conveyor 76 or sent to a safe area with appropriate alarms of the desired type. With questionable signals, the vapor detection module remains closed and a retest is immediately initiated. Retests could even be extended to a two minute cycle to increase the detection sensitivity. Such procedures should reduce the number of false positives that would otherwise be obtained.

Host Computer

The purpose of the host computer is to oversee the whole operation, communicate between operations and maintenance personnel and the system, communicate with existing airline/airport scheduling computers, maintain records, down load programs or update information to the PLC and IMS sensor computer, prepare reports, report faults, report alarms, etc.

For this purpose, an environmentally ruggedized version of the IBM PC/AT or of the DEC micro VAX, operating with large, hard disk storage capacity, may be employed. Exemplary versions of these machines are:

Allen-Bradley, Model 6122 (IBM/aT)
Codar Technology (micro VAX)
Dyna Five Corporation (micro VAX)
MBD Systems, Inc. (micro VAX)
Sigma Information Systems, Industrial Disk Drives and Housings for DEC equipment In the classification area 66, the baggage is sized by an array of photo cells and the data is sent to the PLC. Additionally, if bar code destination readings of baggage bar codes is desired, they are performed and this point with the routing data obtained being transmitted to the PLC. Size reading is done within a ten millisecond time frame, baggage position on the conveyor is determined within inches and, if required, bar code reading is effected within twenty to fifty milliseconds.

The classification area requires approximately three feet of length along an existing baggage conveyor at the entrance of the system.

Each bag is tracked throughout the system by the PLC. Encoders are used on each conveyor to determine the position/velocity of each conveyor and the position of each piece of luggage is updated each twenty milliseconds by the PLC. Photo cells at the beginning of each conveyor confirm the presence of each bag, adjust for slippage or allow the PLC to alarm should a bag be missing due to falling off of the conveyor. In addition, extra bags, placed randomly on the belt in the middle of the system will be identified, rerouted and classified.

Baggage will be transferred from the incoming conveyor 67 to the selected queuing conveyor 70 by centerline pushers 68. The centerline pushers are activated at the appropriate time when the MSR indicates a cell destination/baggage position match and when a positioned photo cell on the centerline pusher indicates that the exact bag centerline has arrived at a predetermined position for pusher contact. The combination of MSR trip and photo cell length measurement at each pusher assures:

(1) Centerline push is made on target (allowance for bag slippage);
(2) The appropriate bag is lined up and dispatched to the appropriate module;
(3) Missing bags are alarmed; and,
(4) Extra bags are alarmed and rerouted.

Control of the detection module in 72 may be effected under a drum timer subroutine in the PLC software. This routine introduces the luggage into the detection module, closes the door, controls the cyclic vacuum/pressure cycle, actuates the valves of the associated vapor collector, controls power pulses to heat the vapor collector surfaces and evolves the trapped vapors, opens the outgoing doors and removes the baggage to the outgoing queuing conveyor 74.

In a system with ten detection modules, drum time subroutines are initiated in six second intervals to maintain synchronization to the vapor detector. The PLC varies the starting sequence for each module to compensate for jammed lines, out of service modules, or retest decisions.

Detector modules are approximately sized for diverse baggage traffic. In a ten module system, five modules may be similarly sized to accommodate the largest average bag, such as a two-suiter. Several modules are smaller, handling briefcases, small packages, shoulder bags and the like. Several modules are larger to handle trunks, over-sized baggage or extra-large packages.

Alternative Embodiment of Vapor Collector

Figure 15:
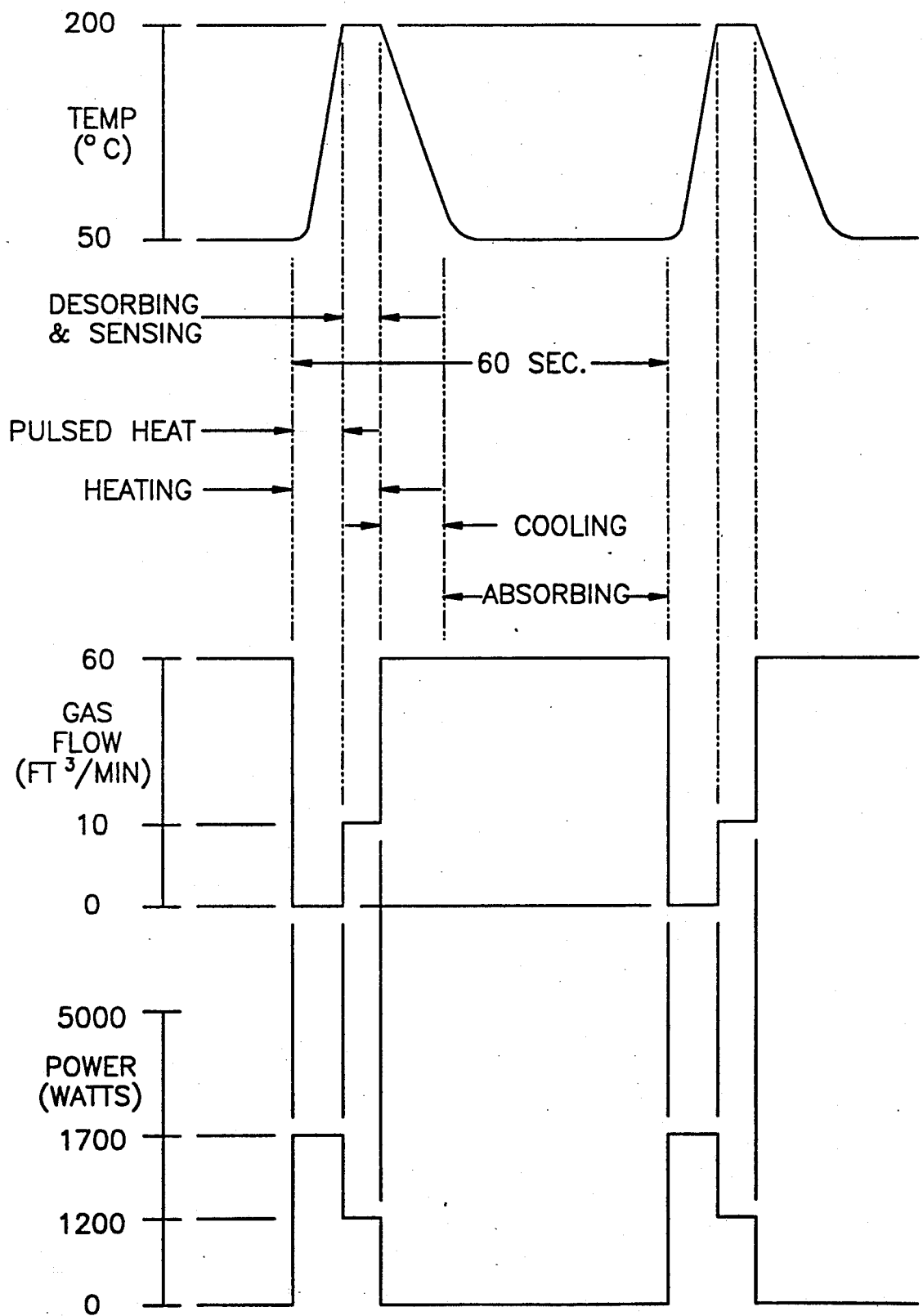
FIG. 15 are temperature, gas flow, and power profiles of an alternate vapor collector design.

An alternative preferred embodiment of vapor collector in which thermal equilibrium is established within a fraction of a second during rapid transition from adsorption to desorption of the explosive molecules from the vapor collector is illustrated in FIGS. 16A, B, and C. The temperature cycling of this vapor collector is shown in FIG. 15. The desorption temperature is held for six seconds by continued direct heating. The transition from the desorption temperature to the adsorption temperature takes place with the module/cell circulation in under six seconds as the heat is dumped into the module and bag.

As shown in FIGS. 16A and B, "sheets" 77 of silicon oxide coated steel are directly heated, using the main AC power source controlled by solid state relays (FIGS. 18A, B), and are supported in ceramic supports 78, 78 by rods 79, 80. The leads are sufficiently conductive to dissipate less than one percent (1%) of the power.

The "sheets" 77 of the vapor collector are held under constant tension by springs 81 biasing the rods 79 to compensate for expansion-contraction during heating and cooling. Tests on the 0.0001" (one ten-thousandths inch) thick stainless steel sheets indicate that they will not vibrate or hum at flows of up to 20 cfm per one square inch of face, which is a total across the vapor collection of $20 \times 4 \times 12 = 1000$ cfm. This number is a factor of about 20 greater than the design values which need be used.

The vapor collector comprises forty parallel "sheets", 10 cm by 30 cm, which sheets are spaced 0.25 cm apart in a volume of 10 cm × 10 cm × 30 cm (3,000 cubic centimeters) and provide a total absorption area of 26.7 square feet with an absorption volume of 0.11 cubic feet. The sheet thickness is 0.0001 inches (one ten-thousandth) and the sheets 77 are covered with a fractional micron thick coating of silicon dioxide on both sides. A long continuous web of foil is used to form the individual sheets by looping it back and forth between the rods 79 and 80 (see FIGS. 16 and 17). Each continuous strip forms a set of twenty sheets and there are two such sets, to form forty sheets. Each set of twenty sheets has a conducting lead at each end to permit direct heating using a solid state controller operating from the 220 volt power source. The tension by compression springs 81 within the rod support posts 71 is applied to the rods, a spring located in both the upper rods opposite the electrical lead connection and lower rod supports 78.

Using air flows, the pressure drops were measured in a forty layer array with spacing of approximately 0.050" apart. The flow resistance was less than 0.1 inch water column 0.004 psig) for a flow of 100 cfm, a pressure drop which is very small and acceptable. Using a 0.0001" foil sample, no hum or noise occurred at flows as high as 1000 cfm.

Temperature cycling produces a change in length of the sheet which is compensated in accordance with the invention by the spring biasing of the support rods. Stainless steel has a coefficient of linear expansion of 10 microinches per inch per degree Celsius. For a 200° C. change, the extension in a twelve inch length of sheet is 0.024 inches (i.e., $10 \times 10^{-6} \times 12 \times 200$). The rod 79 is in a slot of length 0.015" and under spring tension (one pound) (of 0.5 pounds per inch of edge) which in turn pulls on the sheet to keep it flat, as shown in FIGS. 16A-C.

The foils are operated vertically, with down-flowing air, to keep dust from settling on the foils. The signal air is filtered. Th baggage air is ambient air. It is to be expected that heavy molecular weight chemicals may collect on the foils in spite of the normal temperature cycling. An activation cycle to heat the foils, to say 250° C. or even 300° C., is useful to clean up the foils on an automatic regular basis.

Figure 18A:
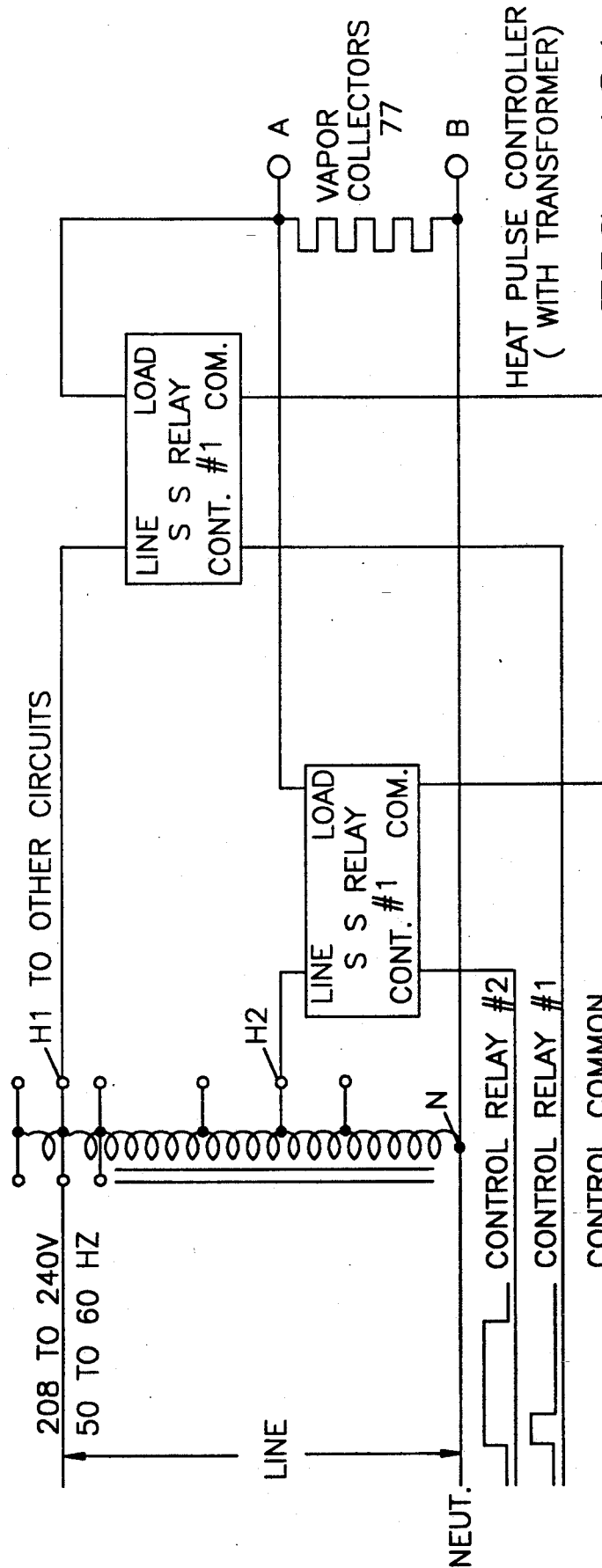
FIG. 18A is a schematic of a heat pulse controller and transformer for the vapor collector.

FIGS. 18A and B show two arrangements for supplying the required power pulses to the vapor collector assembly of FIG. 16A-C to evolve the absorbed explosive molecules. The solid state relays are:

Activated by a TTL level DC voltage;
Rated 25 amperes at 240 volts AC;
Zero Voltage Turn On type;
Zero Current Turn Off type;
Optically isolated; and
Designed to minimize RFI and EMI emissions.

In FIG. 18A, Relay 1 is activated for the desired time interval, e.g., one second, providing the high wattage power pulse from the 208 to 240 volt line. Since the maximum turn-off time is 8.33 msec at 60 Hz (10 msec at 50 Hz), neither relay is activated for 12 msec. Thereafter, Relay 2 is activated, providing the low wattage power to maintain the temperature of the vapor collector surface for the desired time interval, e.g., five seconds, while the sensor gas flow is present. The autotransformer configuration provides low losses, small size and may have several taps to adjust each power level.

Figure 18B:
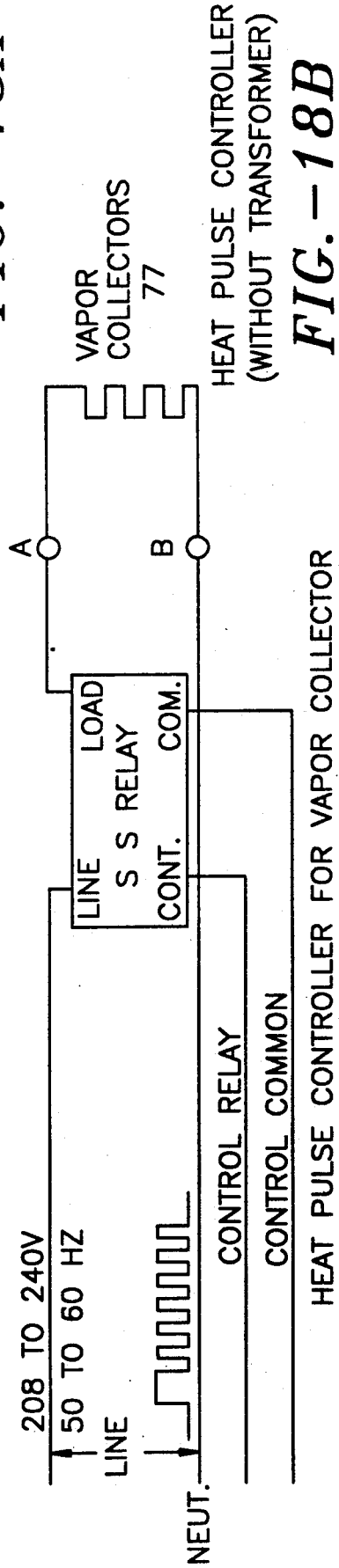
FIG. 18B is a schematic of a heat pulse controller without a transformer for the vapor collector.

In FIG. 18B, an alternate circuit is shown, wherein the reduced power level is obtained by pulsing the solid state relay ON for single, half-cycle intervals of the AC line. For a 60 Hz line, each power ON pulse is 8.33 msec and each power OFF pulse is an integer multiple of 8.33 msec. For 50 Hz lines, the pulses are multiples of 10.0 msec. The programmable logic controller (PLC) can readily synchronize the ON pulses to the line frequency.

A third control arrangement may be used with FIG. 18B, if each vapor collector assembly contains a small, fast response thermocouple. A simple ON-OFF control amplifier supplies the control pulses and maintains the temperature profile of the vapor collector surface within approximately 1° C. of the desired holding temperature. If required, more complex temperature profile may be readily augmented by the PLC.

After the explosive vapor is swept into the sensor 23, the unit must be cooled back to a lower temperature of less than 80° C. for the next cycle of adsorption. The cooling rate is about 1200 watts/15 cfm $\times$ 60 cfm, about 4800 watts. Since there is approximately 17 watt-sec stored in the sheets, the assembly will cool in seconds in an exponential manner. The heat is deposited in the module/cell walls and air ducts and eventually into the baggage area as the module is opened for loading.

It is to be understood that the method and apparatus disclosed hereinabove for rapid detection of explosive materials by trace vapor detection using ion mobility spectrometry has been made by way of broad example only. It will be apparent to those skilled in the art that many further specific modifications to the abovedisclosed method and apparatus may be made without departing from the broad principles of the present invention which shall be limited only to the scope of the appended claims.

In that regard, it is to be understood that the apparatus of the invention and the methods specifically disclosed for detecting traces of explosive vapor may be employed with efficacy for detecting and/or monitoring contaminants from toxic waste dumps and other sources. Thus, the apparatus of the invention may be readily modified for monitoring the perimeter about a point source of toxic air emission monitoring signal. As in the case for testing for explosives, the concentration utilized for toxic waste monitoring would be approximately one part per trillion.

It is to be further understood that the critical elements in carrying out the method of detection in the above-described systems include the vapor collector constructions and the large volume ion mobility spectrometer (LRVIMS-the Model LRV-2 Ion Mobility Spectrometer available commercially from PCP, Inc., West Palm Beach, Florida). Apparatus employing such equipment provides excellent, very low threshold signals while handling a large flow, i.e., one to ten cubic feet per minute (CFM). This apparatus may be used in even greater flows up to approximately 100 CFM as desired and found necessary for a particular application.

An important structural feature of the vapor collection apparatus of the present invention is the employment of multiple and closely spaced surfaces described hereinabove as parallel "sheets". These surfaces may also be in the form of foils, tubes, or the like made from electrically conductive materials which are susceptible to rapid heating when energized by an electrical current. In each variant, the closely spaced vapor collector walls function to collect vapor by adsorption or other physical mechanisms such as condensation or solution from a rapid flow of air or other gas while these surfaces are unheated and at an ambient temperature. The collector surfaces are then rapidly heated by direct conduction to evolve in a selective manner the targeted material or targeted materials in the original gas stream or in an alternate gas stream.

Advantageously, the collector surfaces which are closely spaced are arranged vertically and the air flow through and past those surfaces goes from the top to the bottom of the vapor collector structure as a means of avoiding and/or minimizing the collection of dust on the collector surfaces. As a means of avoiding undue stresses on the collector surfaces and to accommodate the expansion and contraction of the surfaces during the temperature cycling as the surfaces are heated and cooled, the collector "sheets" or other elements are appropriately supported by resilient spring elements and are insulated one from the other so that they may be quickly and efficiently heated electrically. It is to be understood that the foils or tubes or collector surfaces may be fabricated from materials other than stainless steel, as described hereinabove, and the selected material may be plated with other metals, nonmetals, or oxides to accomplish a specific vapor selection.

FIGS. 20A and 20B illustrate an alternative embodiment for the collector in which a foil surface is utilized. As depicted therein, the closely spaced construction for the collective plates may be accomplished by use of a metal foil formed into a special geometry. Extended stainless steel foil sheet 81, which may be of $6 \times 10^{-4}$ cm thickness, width 15 cm and length 360 cm, coated or non-coated, is paired with a similar sized mesh "sheet" 82, typically formed of 0.1 cm diameter fiberglass threads with a mesh width of 1 cm oriented across the 15 cm width of the foil. The foil/mesh pair is rolled into a cylindrical shape to yield in assembly having a 7.5 cm inner diameter and a 9 cm outer diameter. The mesh separates the foil turns and provides the passageway for the airflow through the unit.

As used herein, the term "mesh" is meant to include separator elements formed both of perpendicular strands as well as those having strands extending solely along the axis of the resulting cylinder. The latter construction is preferred, as the flow of air through the cylinder from one end to the other is not impeded. With a cross-mesh construction, allowances must be made for the blocking effect of the crossing strands. This can be done, for example, by providing a thickening at the strand intersections to create a clearance about the intersections, or by using a thinner crossing strand to prevent complete passage blockage.

Electrodes 83 are provided at opposite ends of the cylinder for heating power input. The center core 84 of the cylinder is insulated and closed to prevent airflow therethrough. An outer wrapping cylinder 85, also insulated, supports the assembly.

The vapor collector is, of course, designed for rapid sampling of large volumes of ambient air for the collection of trace condensible chemicals, whether they are explosives, contaminants or other toxic substances. Stated in other terms, the vapor collector 31 acts as an adjustable impedance to match the vapor sensor 23 to the real world environment. The vapor collector thus acts as a concentrator, putting the detected vapor molecules into a smaller gas volume and concentrating the vapor species before it is sensed by the LRVIMS. Stated differently, the vapor collector acts as a separator collecting some species of chemicals with greater efficiency (those targeted) and driving off some interfering chemicals earlier or later than the particular chemical sought to be screened or otherwise detected.

It will be understood that in certain applications the vapor collectors may be cascaded when desired or necessary to concentrate further the targeted chemicals, to eliminate interferents and change carrier gases for specific use with optimum detector technology. Moreover, it is contemplated that the new vapor collectors may be used in some instances with other chemical vapor sensors than the LRVIMS described herein. It will further be appreciated that condensible vapors, aerosols, and fine particulates, as well as gases, may be collected by the vapor collectors of the present invention. It is to be appreciated that the structure of these new and improved vapor collectors is particularly applicable for collecting high molecular weight vapors from explosives, such as TNT, RDX and the like, as well as carcinogens like dioxins, PCBs and the like. Indeed, volatile materials such as chlorinated fluorocarbons are also collectible. As mentioned immediately hereinabove, the special surfaces on the vapor collector or from which the vapor collector is constructed are chosen to optimize the efficiency of the collector for the purpose of targeting the chemical of interest against the large background of potential interferent chemicals.

It should be understood, of course, that the various forms of the invention herein illustrated and described are intended to be representative only, as certain changes may be made therein without departing from the clear teachings of the disclosure. Accordingly, reference should be made to the following appended claims in determining the full scope of the invention.

We claim:

1. Apparatus for the detection of the presence of selected materials in an object by the extraction and analysis of vapor samples therefrom, comprising a sampling chamber adapted to accept the object; means for removing a portion of the vapor contents from the object and blending said removed portion with the surrounding atmosphere in said sampling chamber; means for collecting the molecules of the selected materials from said mixture to create a test sample wherein the concentration of said molecules is substantially above the initial vapor concentration thereof; and means for performing an analysis upon said test sample whereby the presence of said selected material is determined.

2. The apparatus of claim 1, wherein said sampling chamber comprises a sealed chamber of variable volume.

3. The apparatus of claim 1, wherein said vapor contents removing means comprises means for varying the pressure within said chamber.

4. The apparatus of claim 3, wherein said blending means comprises said means for varying the pressure within said chamber.

5. The apparatus of claim 4, wherein said means for varying the pressure varies the pressure between about ten percent above and below ambient.

6. The apparatus of claim 4, wherein said means for varying the pressure comprise means for varying the volume of said chamber.

7. The apparatus of claim 6 further comprising means for coupling said collection means to said sampling chamber solely during the time said blending means is in operation.

8. The apparatus of claim 6, wherein said coupling means includes means for circulating the atmospheric contents of said sampling chamber through said collection means during the time said blending means is in operation.

9. The apparatus of claim 5, wherein said means for varying the volume of said chamber comprise a chamber wall in the form of a bellows.

10. The apparatus of claim 9, wherein said bellows is operated pneumatically.

11. The apparatus of claim 8, wherein said collection means comprises an adsorbent for the molecules sought to be sensed.

12. The apparatus of claim 9, further comprising means for decoupling said collection means from said chamber at the end of the blending cycle and for coupling said collection means to said analysis means.

13. The apparatus of claim 12 further comprising means for removing said molecules from said adsorbent and transferring said molecules to said analysis means.

14. The apparatus of claim 12, wherein said removal means comprises an adsorbent heater to evaporate said molecules from said adsorbent and blower means for transferring said evaporated molecules to said analysis means.

15. A method for determining the presence of vapors a selected substance within closed baggage and the like, comprising the steps of
   a) placing the baggage item within a sealed sampling chamber;
   b) extracting at least a portion of the gaseous contents of the baggage to the exterior of the baggage, whereby such contents is mixed with the atmosphere within said chamber;
   c) collecting the molecules of the desired substance from said mixture to create a sample, wherein the concentration of said molecules is substantially above the initial vapor concentration thereof; and
   d) analyzing said sample to determine the presence of said selected molecule.

16. The method of claim 15, wherein said extraction step comprises lowering the pressure within said chamber to cause the passage of a portion of the vapor-containing gaseous contents of the baggage to the exterior of the baggage.

17. The method of claim 15, wherein said lowering of pressure is part of a pressure cycle including a step wherein the pressure within said chamber is increased above ambient.

18. The method of claim 17, wherein said pressure cycle is repeated on a periodic basis.

19. The method of claim 17, wherein said pressure cycle is performed by oscillation of a wall of the chamber.

20. The method of claim 15, wherein said collection step is performed concurrently with said extraction step.

21. The method of claim 20, wherein said mixing step includes the continuous circulation of the contents of said chamber between said chamber and a remote molecule adsorber.

22. The method of claim 21 further including the steps of isolating said molecule adsorber from said chamber then transferring said molecules from said adsorber to an analysis means before said analysis is performed.

23. The method of claim 21, wherein said transfer from said adsorber is performed by heating said adsorber and creating an air flow between said adsorber and said analysis means.

24. The method of claim 15, wherein said sample collection step comprises collecting the molecules on a first adsorbent within a first volume, desorbing the adsorbed molecules and adsorbing them on a second adsorbent within a second volume less than said first volume to provide a more concentrated molecule sample.

25. A vapor collector comprising a housing having an inlet at a first side and an outlet, a ribbon-like molecule collector means arranged within said housing in a layered manner, and means for circulating vapor-containing gas across the molecule collector means.

26. The vapor collector of claim 25, wherein said ribbon molecule collector means is formed of nichrome sheets coated with silicon dioxide.

27. The vapor collector of claim 26, wherein said ribbons are arranged in 20 layers, each of said layers comprising 4 parallel ribbons.

28. The vapor collector of claim 27, wherein each of said ribbons is spring-mounted to said chamber.

29. The vapor collector of claim 26 further including means for heating said nichrome sheets to a temperature in excess of about 150 degrees C. to desorb collected molecules from said sheets.

30. The vapor collector of claim 26, wherein said heating means is an electric power source connected to said nichrome sheets.

31. The vapor collector of claim 29 further including means for transferring said desorbed molecules to a remote detector.

32. The vapor collector of claim 31, wherein said transfer means comprises a blower.

33. The vapor collector of claim 25 wherein said molecule collector is in the form of a spiral winding of an electrically conductive material, the turns of said winding being spaced from each other.

34. The vapor collector of claim 33 wherein said spiral winding is of foil.

35. The vapor collector of class 34 wherein said foil is of stainless steel.

36. The vapor collector of claim 34 wherein the turns of said spiral winding are separated by an insulating medium.

37. The vapor collector of claim 36 when said insulating medium is a mesh adapted to permit said vapor-coating gas to pass between said turns.

38. The vapor collector of claim 37 where said mesh comprises a plurality of parallel strands aligned with the axis of said spiral winding.

39. Apparatus for the analysis of baggage and the like for the presence of predetermined vapors, comprising
   a baggage-analysis module comprising a first baggage-acceptance compartment and a second compartment, said first and second compartments being joined by a flexible, piston-forming wall;
   means for loading baggage into said first compartment for analysis and subsequently removing it therefrom;
   means for transferring at least a portion of the air from said first compartment to a vapor collector chamber;
   a vapor collector array located with said vapor collector chamber for collecting molecules of the predetermined vapors;
   means for removing the molecules of the predetermined vapors from said collector and transferring same to a vapor sensor;
   a vapor sensor for the analysis of said molecules; and
   means for varying the pressure within said second compartment whereby said piston-forming wall is driven to cause pressure variation within said first compartment to extract vapors from the interior of baggage placed therein and combine said vapors with the air of said first compartment.

40. The apparatus of claim 39, wherein said transfer means comprise a blower and valve operatively connected to said first compartment.

41. The apparatus of claim 39, wherein said vapor collector array comprises adsorbant sheets for the molecules of the predetermined vapors and said means for removing the molecules from said collector comprises means for raising the temperature of said adsorbant to cause the release of the vapor molecules therefrom.

42. The apparatus of claim 41, wherein said adsorbant sheets comprise a silicon dioxide coating applied to a substrate.

43. The apparatus of claim 42, wherein said substrate is nichrome.

44. The apparatus of claim 42, wherein said means for raising the temperature of said adsorbant comprises means for applying an electric potential across said nichrome sheets.

* * * * *